US011633879B2

(12) United States Patent
Stoeckl et al.

(10) Patent No.: US 11,633,879 B2
(45) Date of Patent: Apr. 25, 2023

(54) ANATOMIC TISSUE-ENGINEERED OSTEOCHONDRAL IMPLANT AND METHOD FOR FABRICATION THEREOF

(71) Applicants: United States Government as Represented by the Department of Veterans Affairs, Washington, DC (US); THE TRUSTEES OF THE UNIVERSITY OF PENNSYLVANIA, Philadelphia, PA (US)

(72) Inventors: Brendan D. Stoeckl, Philadelphia, PA (US); Robert L. Mauck, Philadelphia, PA (US); Hannah Zlotnick, Philadelphia, PA (US); Megan Farrell, Philadelphia, PA (US); Liane Miller, Philadelphia, PA (US); David Steinberg, Philadelphia, PA (US)

(73) Assignees: United States Government As Represented By The Department of Veterans Affairs, Washington, DC (US); The Trustees Of The University Of Pennsylvania, Philadelphia, PA (US)

( * ) Notice: Subject to any disclaimer, the term of this patent is extended or adjusted under 35 U.S.C. 154(b) by 152 days.

(21) Appl. No.: 17/152,647

(22) Filed: Jan. 19, 2021

(65) Prior Publication Data
US 2021/0221030 A1    Jul. 22, 2021

Related U.S. Application Data

(60) Provisional application No. 63/039,089, filed on Jun. 15, 2020, provisional application No. 62/963,892, filed on Jan. 21, 2020.

(51) Int. Cl.
B29C 33/38    (2006.01)
B33Y 10/00    (2015.01)
(Continued)

(52) U.S. Cl.
CPC ...... *B29C 33/3842* (2013.01); *A61F 2/30942* (2013.01); *A61F 2/4261* (2013.01);
(Continued)

(58) Field of Classification Search
CPC .................................................. B29C 33/3842
See application file for complete search history.

(56) References Cited

U.S. PATENT DOCUMENTS 6,103,255 A    8/2000 Levene
6,306,424 B1    10/2001 Vyakarnam
(Continued)

OTHER PUBLICATIONS

Roach et al. Fabrication of tissue engineered osteochondral grafts for restoring the articular surface of diarthrodial joints. Methods: Aug. 2015. 84. pp. 103-108 (Year: 2015).*
(Continued)

*Primary Examiner* — Cachet I Proctor
(74) *Attorney, Agent, or Firm* — Ballard Spahr LLP

(57) ABSTRACT

A method for forming a prosthesis comprising a bone-like portion and a cartilage-like portion can comprise additively manufacturing a first positive mold in accordance with a portion of a first three-dimensional model of a portion of a bone. A first negative mold can be formed from the first positive mold. The bone-like portion can be created within the first negative mold. A second positive mold of the bone and a cartilage can be additively manufactured from a second three-dimensional model. A portion of the second three-dimensional model can correspond to a portion of the first three-dimensional model. A second negative mold can be formed from the second positive mold. The bone-like portion can be positioned in the second negative mold so that the second negative mold and the bone-like portion can define a cartilage space that can be filled with a material to form the cartilage-like portion of the prosthesis.

25 Claims, 19 Drawing Sheets

(51) Int. Cl.

| | |
|---|---|
| *B33Y 50/00* | (2015.01) |
| *B33Y 80/00* | (2015.01) |
| *A61F 2/30* | (2006.01) |
| *A61F 2/42* | (2006.01) |
| *A61L 27/18* | (2006.01) |
| *A61L 27/52* | (2006.01) |
| *A61L 27/26* | (2006.01) |
| *B29C 64/386* | (2017.01) |
| *B29K 67/00* | (2006.01) |
| *B29K 105/00* | (2006.01) |
| *B29L 31/00* | (2006.01) |

(52) U.S. Cl.
CPC .............. *A61L 27/18* (2013.01); *A61L 27/26* (2013.01); *A61L 27/52* (2013.01); *B29C 64/386* (2017.08); *B33Y 10/00* (2014.12); *B33Y 50/00* (2014.12); *B33Y 80/00* (2014.12); *A61F 2002/30948* (2013.01); *A61F 2002/30952* (2013.01); *A61F 2002/30953* (2013.01); *A61F 2002/30957* (2013.01); *A61F 2002/30985* (2013.01); *A61F 2002/4271* (2013.01); *A61L 2430/02* (2013.01); *A61L 2430/06* (2013.01); *B29K 2067/04* (2013.01); *B29K 2105/0061* (2013.01); *B29K 2883/00* (2013.01); *B29L 2031/7532* (2013.01)

(56) References Cited

U.S. PATENT DOCUMENTS

| | | | |
|---|---|---|---|
| 6,773,713 B2 | 8/2004 | Bonassar et al. | |
| 7,446,131 B1 | 11/2008 | Liu | |
| 8,637,065 B2 * | 1/2014 | Athanasiou | C12N 5/0655 435/402 |
| 8,734,824 B2 | 5/2014 | Bennett | |
| 8,858,631 B2 | 10/2014 | Seifalian | |
| 8,974,535 B2 | 3/2015 | Antonyshyn | |
| 9,155,818 B2 | 10/2015 | Tampieri | |
| 9,693,873 B1 * | 7/2017 | Sand | A61L 27/12 |
| 9,833,481 B2 | 12/2017 | Muneoka | |
| 9,907,663 B2 | 3/2018 | Patrick et al. | |
| 2004/0167390 A1 * | 8/2004 | Alexander | A61B 5/112 600/410 |
| 2005/0074877 A1 | 4/2005 | Mao | |
| 2011/0256628 A1 | 10/2011 | Galperin | |
| 2015/0075699 A1 | 3/2015 | Smith | |
| 2016/0256246 A1 | 9/2016 | Stapleton | |
| 2016/0287407 A1 * | 10/2016 | Patrick | A61F 2/4618 |
| 2017/0333597 A1 * | 11/2017 | Bhumiratana | A61L 27/425 |
| 2018/0289493 A1 | 10/2018 | Mansmann | |
| 2019/0119462 A1 | 4/2019 | Desai | |
| 2019/0134276 A1 | 5/2019 | Spiller | |

OTHER PUBLICATIONS

Stoeckl et al. Engineered Anatomic Implants Restore Geometry and Load Transfer in the Porcine Accessory Carpal Joint. University of Pennsylvania Orthopaedic Journal, pp. 110-112. Jun. 2020 (Year: 2020).*

Stoeckl et al. Design and Implantation of an Engineered Porcine Accessory Carpal Osteochondral Unit. University of Pennsylvania Orthopaedic Journal. pp. 117-118. Jun. 2019 (Year: 2019).*

* cited by examiner

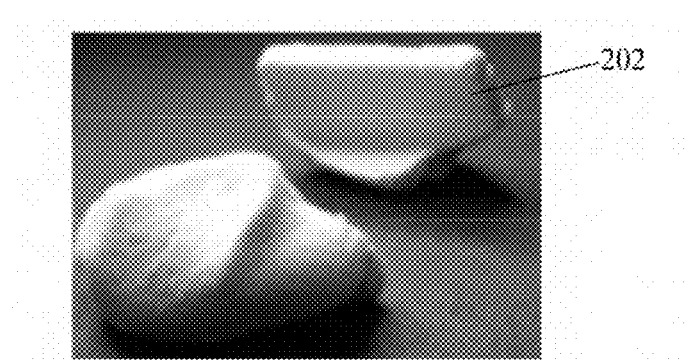
FIG. 19
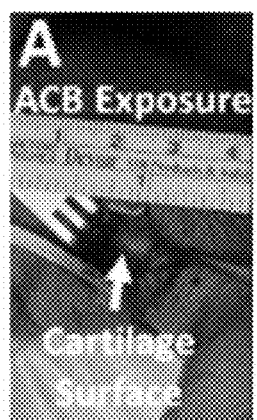 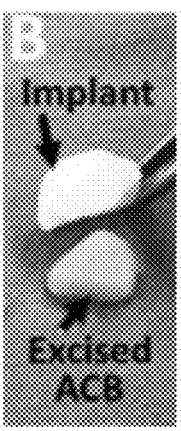 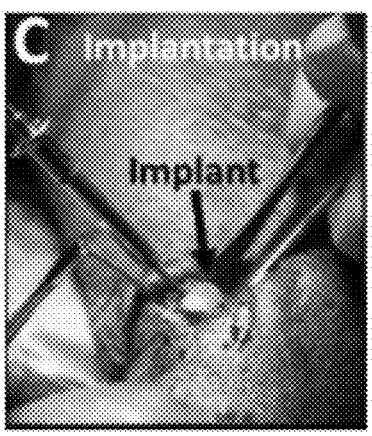 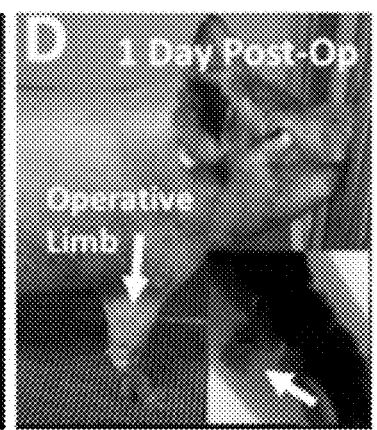
FIG. 20A  FIG. 20B  FIG. 20C  FIG. 20D
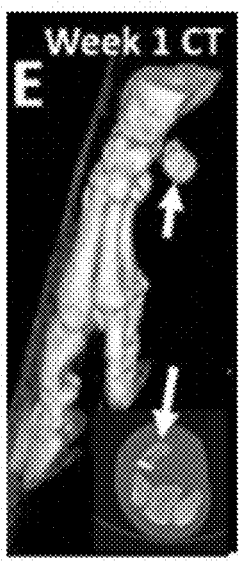 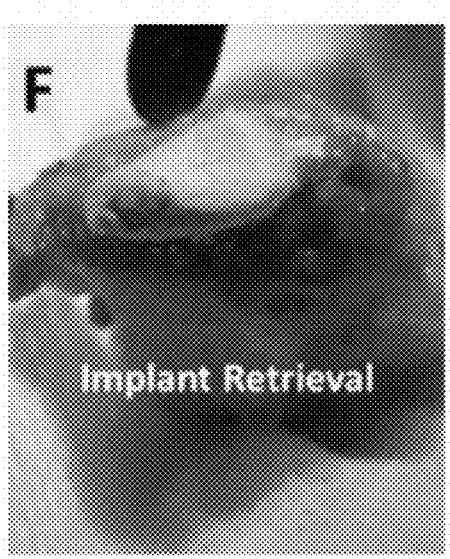 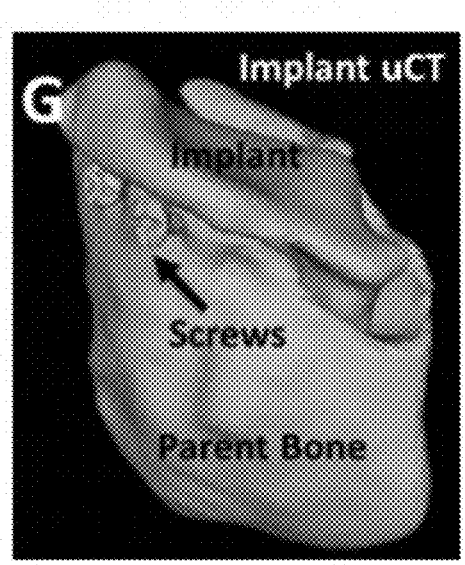
FIG. 20E  FIG. 20F  FIG. 20G

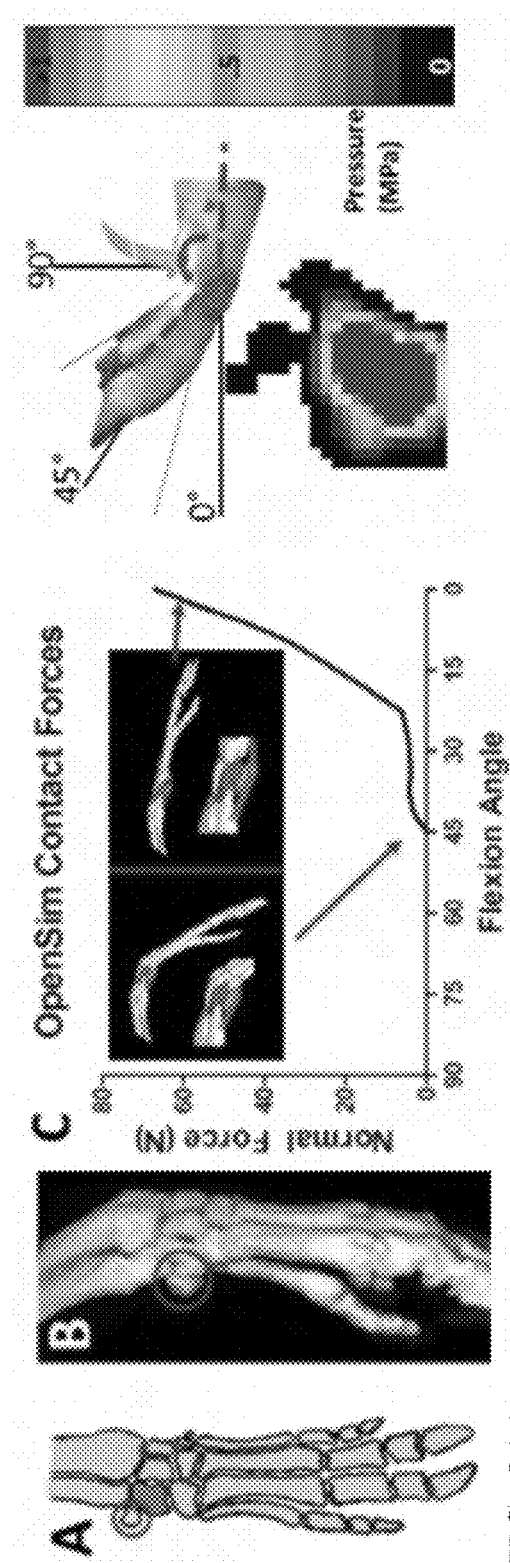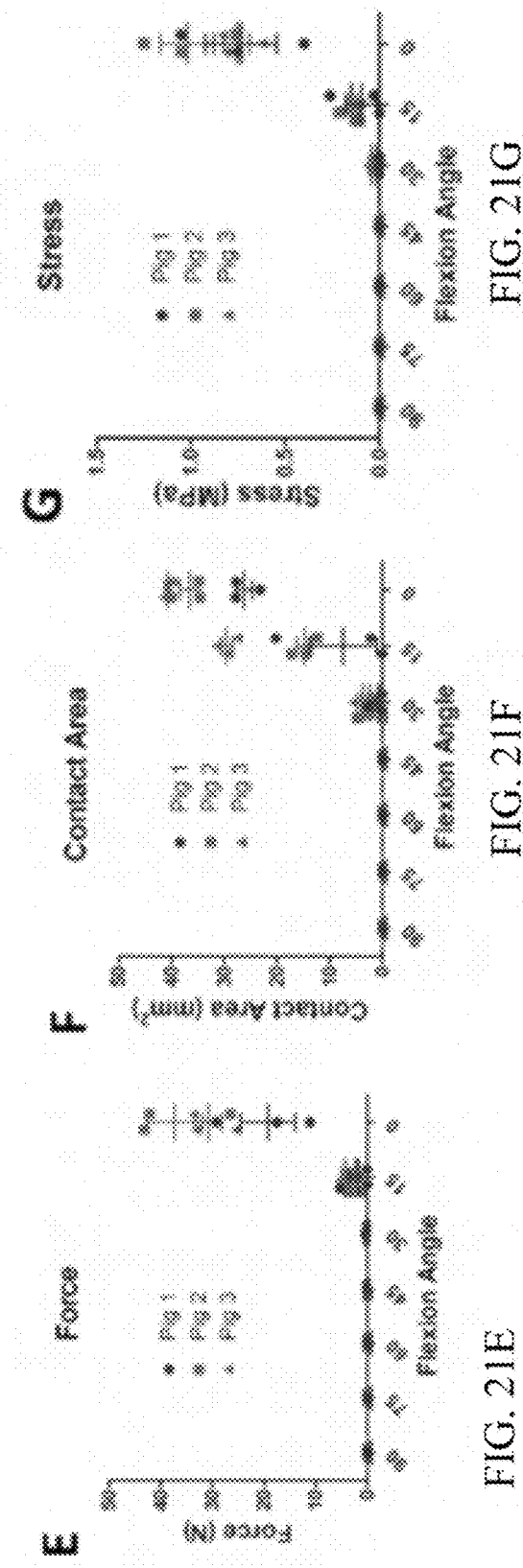
FIG. 21A  FIG. 21B
FIG. 21C
FIG. 21D
FIG. 21E
FIG. 21F
FIG. 21G

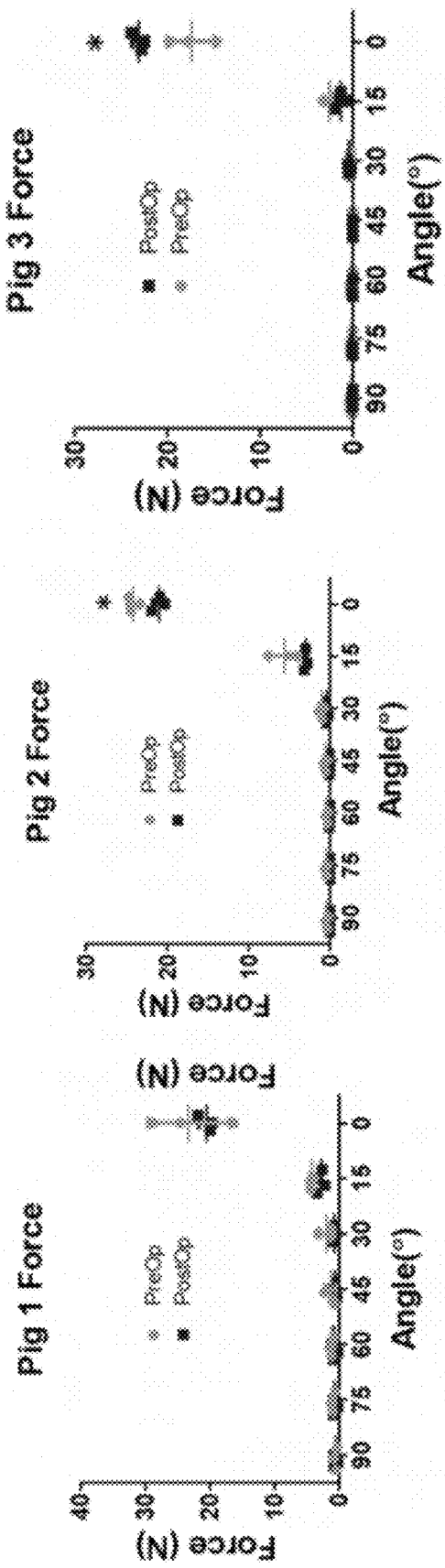
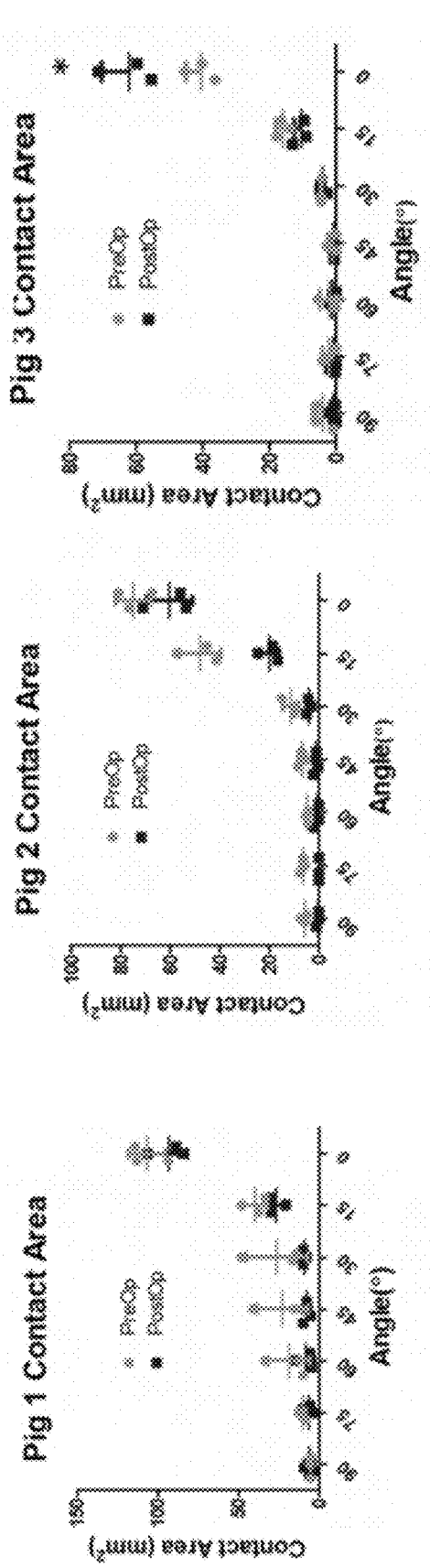
FIG. 24A  FIG. 24B  FIG. 24C
FIG. 24D  FIG. 24E  FIG. 24F

ANATOMIC TISSUE-ENGINEERED OSTEOCHONDRAL IMPLANT AND METHOD FOR FABRICATION THEREOF

CROSS-REFERENCE TO RELATED APPLICATION

This application claims priority to and the benefit of the filing date of the following applications: U.S. Provisional Patent Application No. 62/963,892, filed Jan. 21, 2020; and U.S. Provisional Patent Application No. 63/039,089, filed Jun. 15, 2020. The entireties of these applications are hereby incorporated by reference herein.

STATEMENT OF GOVERNMENT SUPPORT

This invention was made with government support under R01 EB008722 awarded by the National Institutes of Health and under I01 RX000700 awarded by the Department of Veteran Affairs. The government has certain rights in the invention.

FIELD

This application relates to implants comprising a bone-like material and a cartilage-like material.

BACKGROUND

Trapeziometacarpal (TMC) osteoarthritis (OA) is one of the most common conditions affecting middle and older aged adults. Conservative treatments often fail in the long term, and many patients will eventually require destructive surgical intervention involving removal of all or part of the trapezium and replacement with tendon, fascia, or an artificial implant. While effective at reducing pain, these procedures compromise grip strength and can result in subsidence and disfigurement of the hand.

SUMMARY

Disclosed herein, in one aspect, is a method for forming a prosthesis comprising a bone-like portion and a cartilage-like portion. The method can comprise additively manufacturing a first positive mold in accordance with at least a portion of a first three-dimensional model of at least a portion of a bone. A first negative mold can be formed from the first positive mold. The bone-like portion of the prosthesis can be formed within the first negative mold. A second positive mold of the bone and a cartilage can be additively manufactured from a second three-dimensional model, wherein a portion of the second three-dimensional model corresponds to a portion of the first three-dimensional model. A second negative mold can be formed from the second positive mold. The bone-like portion of the prosthesis can be positioned in the second negative mold so that the second negative mold and the bone-like portion of the prosthesis define a cartilage space. The cartilage space can be filled with a material to form the cartilage-like portion of the prosthesis.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 19 is a prosthesis formed in the mold of FIG. 18.

FIGS. 20A-20G illustrate steps for implanting a prosthesis into an animal test subject.

FIGS. 21A-21G illustrate simulations performed in evaluating prostheses in accordance with the present disclosure.

FIGS. 24A-24C illustrate force measurements across flexion angles for each of 3 pigs before and after implantation of composite implant. FIGS. 24D-24F illustrate the respective contact areas for each of the three pigs.

DETAILED DESCRIPTION

Figure 1A:
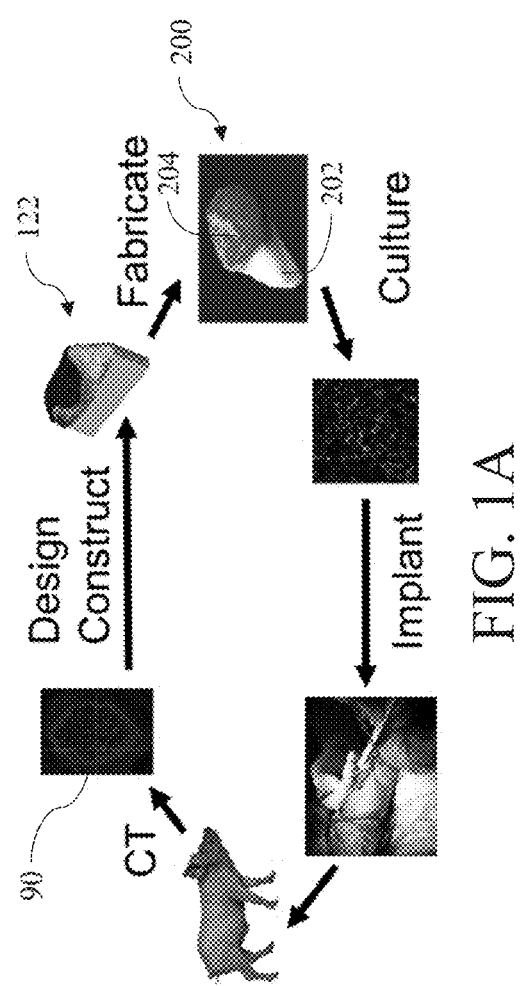
FIG. 1A is a flowchart illustrating a method of making a prosthesis as disclosed herein.

The disclosed system and method may be understood more readily by reference to the following detailed description of particular embodiments and the examples included therein and to the Figures and their previous and following description.

It is to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural references unless the context clearly dictates otherwise. Thus, for example, reference to "a keel" includes one or more of such keels, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Optionally, in some aspects, when values are approximated by use of the antecedents "about," "substantially," or "generally," it is contemplated that values within up to 15%, up to 10%, up to 5%, or up to 1% (above or below) of the particularly stated value or characteristic can be included within the scope of those aspects.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Unless otherwise indicated, in the specification and claims of the following disclosure, it is contemplated that aspects of the disclosure that are described using the word "comprise" or "comprising" (or equivalent language such as "include") can be modified to replace the terms "comprise" and/or "comprising" with "consists of" and/or "consisting of" to provide additional aspects.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification. Thus, words denoting order, such as "first" or "next," should be interpreted as optional aspects unless plain meaning or logic dictates otherwise.

Disclosed herein are methods for the fabrication of anatomically-shaped osteochondral constructs. In some aspects, the constructs can be formed from biomaterials and can optionally be cell-seeded and pre-cultured before implantation in humans or large animals to replace full articulating surfaces.

Referring to FIGS. 1A-3, it is contemplated that for damaged connective tissue 10, such as, for example, a bone 12 having damaged cartilage 14 thereon, a portion 16 of the bone and the cartilage can be removed, and a prosthesis 200 can be implanted into the remaining portion 20 of the bone. The prosthesis can comprise a bone-like portion 202 and a cartilage-like portion 204 so that the remaining portion of the bone and the prosthesis cooperate to form an assembly that mimics a healthy, natural bone and cartilage. Accordingly, in some aspects, the bone and prosthesis assembly can cooperatively define the shape of the recipient's original bone and cartilage prior to wear and damage. In further optional aspects, the bone and prosthesis assembly can cooperatively form an ideal shape that is preferable over the original bone and cartilage prior to wear and damage. For example, it is contemplated that the ideal shape can eliminate structural defects in the original bone. As further described herein, the bone-like portion 202 can be configured to promote integration and ingrowth of bone into the prosthesis.

In some aspects, a method of making the prosthesis 200 can comprise using a medical image to create a three-dimensional model of a bone. At least a portion of the three-dimensional model of the bone can be used to create a three-dimensional model of at least a portion of a prosthesis. The three-dimensional model of the at least a portion of the prosthesis can be used to form a first positive mold of a bone-like portion of the prosthesis and a second positive mold of the bone-like portion and cartilage-like portion of the prosthesis. First and second negative molds can be formed from the respective first and second positive molds. The bone-like portion of the prosthesis can be formed using the first negative mold, and the cartilage can be formed on the bone-like portion of the prosthesis using the second negative mold. As should be understood, and as further described herein, a positive mold can define surfaces that correspond to the surfaces of the desired shape to be formed from the mold (e.g. surfaces of the shape of the prosthesis). The positive mold can be used to form a negative mold from which at least a portion of the prosthesis can be formed. Accordingly, the positive mold can define a receiving space into which a moldable material can be received and cured or hardened to form the negative mold. As should be understood, a negative mold can comprise complementary surfaces to the surfaces of the positive mold so that, when moldable material is received in the negative mold, the moldable material can form the shape of the desired shape.

Figure 6:
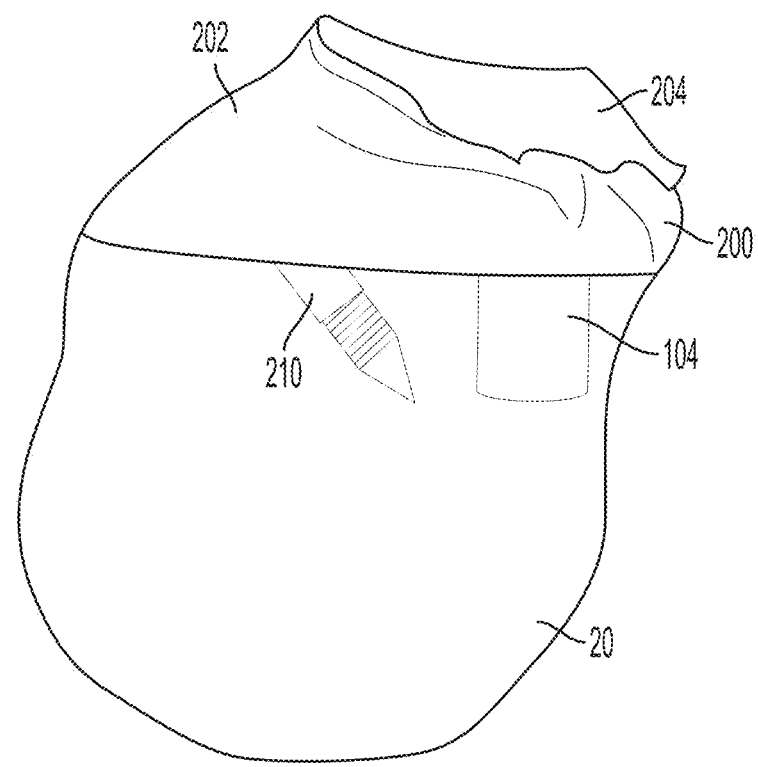
FIG. 6 is a side view of an exemplary prosthesis in accordance with the present disclosure implanted in a bone.

In exemplary aspects, the disclosed fabrication methods can be applied to any osseous or osteochondral anatomy in a human or animal body, such as, for example, a trapezium bone. In further aspects, the disclosed fabrication methods can be applied to forming prostheses for, without limitation, a partial or full femoral condyle in a knee joint, a tibial plateau, a humeral head, glenoid of the scapula, any carpal bone, articular surfaces of the talus or calcaneus, or any other joint. In an exemplary embodiment, and as shown in FIG. 6, a prosthesis 200 for at least a portion of a porcine accessory carpal bone (ACB), which is a sesamoid bone in the forelimb of a pig, can be formed. The ACB can be an approximation of the human trapezium to develop an animal model for its repair or replacement.

In some aspects, the prosthesis 200 can be formed based on an image 90 of at least a portion of a bone. For example, in some aspects, the image can be captured via one of a computed tomography (CT) scan (optionally, a micro computed tomography scan), or a magnetic resonance imaging (MRI) scan. In further optional aspects, the bone (or portion thereof) can be removed from the body, and the image can be captured by a scan (e.g., a laser scan) of the ex vivo bone. In some optional aspects, the bone can be soaked in a solution (e.g., Lugol's solution) to enhance contrast between the cartilage and the background.

Referring to FIGS. 4A-5B, the image of the bone (or the portion thereof) can form the basis for a first three-dimensional model 100 of the bone (or a portion thereof) and a second three-dimensional model 122 of the bone (or a portion thereof) and cartilage thereon. (As used herein, for the sake of conciseness, reference to the "bone" in describing the prosthesis or the first and second models should be understood to include either the entire bone or a portion of the bone, unless context indicates otherwise.) For example, an initial version of the first three-dimensional model of the bone can be created from the image of the bone using software such as, for example, ITK-SNAP, MATERIALIZE MIMICS, or SLICER 3D software. For example, the software can use segmentation to create the three-dimensional model. In some aspects, the first three-dimensional model can be a surface mesh of the bone. Optionally, the surface mesh can be or correspond to an .STL file.

Creating the first three-dimensional model 100 from the image can further comprise modifying the first three-dimensional model from its initial version. In some aspects, the initial version of the three-dimensional model can be cleaned and simplified with the same or another software (e.g., MESHLAB, an open source software). For example, in some aspects, an edge collapse decimation can be performed to reduce a number of faces of the surface of the mesh. Additionally or alternatively, a Laplacian smoothing can be applied to the first three dimensional model. Still further, vertices (e.g., vertices 92) of the first three-dimensional model that correspond to space inside the bone can be deleted, and the surface can be re-meshed (e.g., using a Poisson surface reconstruction). That is, vertices of the surface mesh that, if the surface mesh and the bone were overlaid at a 1:1 scale, would be positioned within the volume of the bone can be deleted, and a new mesh can be formed from the remaining vertices. In exemplary aspects, it is contemplated that the steps of modifying or adjusting the mesh as discussed above can be performed using MESH-LAB software or other software or methods for performing mesh manipulation as is known in the art.

Still further, the surface mesh can be manually edited. For example, a medical professional (and/or a processor (for example, executing program instructions and/or using artificial intelligence)) can detect holes that are inconsistent with an idealized bone, and the medical professional, via software (e.g., optionally, SOLIDWORKS, MESHLAB, or MATERIALIZE MIMICS), can edit the first three-dimensional model to remove (i.e., fill) said holes. Likewise, the medical professional (and/or artificial intelligence) can detect osteophytes that are inconsistent with an idealized bone and, via software, can edit the first three-dimensional model to remove (i.e., fill) said osteophytes. It is contemplated that MATERIALIZE MIMICS software can be beneficially used in that it has the approval of the Food and Drug Administration for 3D printing anatomic models based on human medical imaging.

As stated herein, it is contemplated that a portion of a bone having damaged cartilage thereon can be removed, and the prosthesis can couple to a remaining portion of the bone to replace the removed portion of the bone having damaged cartilage thereon. Accordingly, the bone can have a shape (e.g., a three-dimensional shape). In some aspects, the shape of the bone can be the original shape of the bone prior to having the portion removed. In further optional aspects, the shape of the bone can be a preferred shape over the shape of the original bone (e.g., without holes or osteophytes). The first three-dimensional model can therefore be modified so that a prosthesis having the shape of the first three-dimensional model can mate with the remaining portion of the bone so that the remaining portion of the bone and the prosthesis cooperatively form the shape of the bone (e.g., either the original shape or the preferred shape of the bone).

In some aspects, said modification to adapt the first three-dimensional model to cooperate with the remaining portion of the bone to form the shape of the bone can comprise providing an interface 102 (e.g., a planar surface) on the first three-dimensional model. Said interface can be provided at a select offset from an end of the bone. The interface can be provided relative to an offset axis that can optionally be parallel to the longitudinal axis 18 of the bone. Optionally, the bone can have a length, and the interface 102 can be provided at about one third of the length of the bone 12. It is contemplated that a minimal amount of bone can be removed and replaced with the prosthesis in order to achieve sturdy fixation. In some aspects, the minimum amount can be selected based on the portion of the bone that is damaged or diseased and requires replacement, or a minimum amount to provide a mount for supporting the cartilage-like portion of the prosthesis. In this way, the amount of material added to the body (that the body's cells then penetrate and colonize) can be minimized. Thus, in some aspects, the interface 102 can be provided at less than one half of the length of the bone (e.g., between one half and one fifth of the length). In further aspects, the interface can be provided at less than one centimeter (e.g., about a half of a centimeter) from the end of the bone to be replaced. The location, size, and/or shape of the bone interface can be modified based on the implant site and/or loading expectations after implantation.

In some optional aspects, the first three-dimensional model can be modified (for example, using software as disclosed herein) to define at least one fixation feature. Thus, in these aspects, the first three-dimensional model includes at least one fixation feature as disclosed herein. For example, in some aspects, the fixation feature can be a keel 104. In further aspects the at least one fixation feature can comprise at least one through-hole for receiving a screw. In other aspects, the at least one fixation feature can comprise one or more pegs, one or more keels, a main keel and one or more support struts or keels oriented perpendicularly to the main keel, tabs for surgical manipulation, or combinations thereof.

Figure 8:
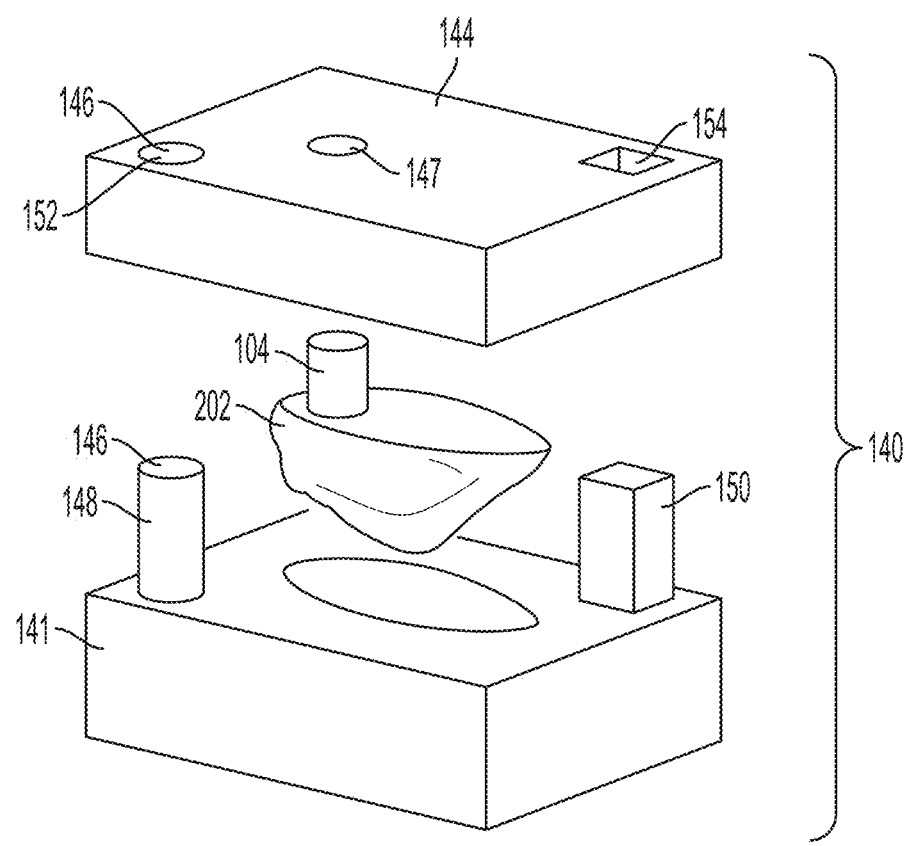
FIG. 8 is an exploded perspective view of the prosthesis of FIG. 6 and a mold for forming the prosthesis.
Figure 22A:
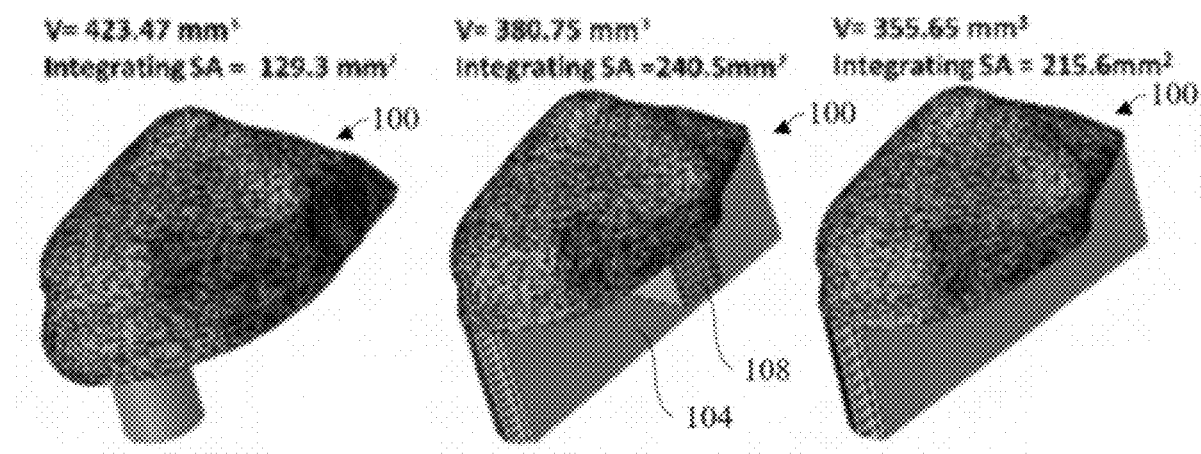
FIG. 22A illustrates perspective views of optional keel structures.

In some aspects, the keel 104 can extend along (optionally, be elongate relative to) a keel axis 106 that can be parallel to the longitudinal axis 18 of the bone. In some aspects the keel axis can be parallel to a longitudinal axis of the bone. As shown in FIG. 8, in some aspects, the keel can be cylindrical. In some optional aspects, the keel can be, for example, about 5 mm long and about 2 mm wide. However, it should be understood that other dimensions can be used depending upon the particular type, location, and shape of the bone. As shown in FIG. 22A, in further aspects, the keel can be elongate relative to a major dimension of the first three-dimensional model. In still further aspects, the keel can comprise one or more support struts 108 (FIG. 22A).

In some optional aspects, it is contemplated that the first three-dimensional model 100 can form the shape of the portion of the prosthesis excluding the keel. Thus, in these aspects, the first three-dimensional model 100 can define the shape of a first positive mold portion, and the keel 104 or other such fixation feature of the prosthesis can be formed via a third positive mold portion so that the first positive mold portion and third positive mold portion can cooperate to ultimately form the shape of the prosthesis (via production of first and third negative molds from the first and third positive molds, as further described herein). Thus, the fixation feature (e.g., the keel 104) can optionally be excluded from the first three-dimensional model. That is, because the portion of the prosthesis excluding the keel or other fixation element can be formed from a mold portion that is separate from a mold portion that forms the keel or other fixation element, the first three-dimensional model need not include the fixation element.

A second three-dimensional model can be a surface mesh of the bone and cartilage thereon. In some aspects, the second three-dimensional model can be made from the first three-dimensional model. Accordingly, the second three-dimensional model can be or correspond to a surface mesh of the bone (e.g., an .STL file).

In some aspects, creating the second three-dimensional model 122 can comprise translating (e.g., using software as disclosed herein) a first portion 124 of the surface mesh of the first three-dimensional model away from a second portion 126 of the first three-dimensional model relative to a translation axis 128. Optionally, the translation axis can be perpendicular to the longitudinal axis of the bone. In exemplary aspects, the translation of the first portion of the surface mesh away from the second portion of the first three-dimensional model can form a space (between the first and second portions) that is configured to receive the cartilage-like portion of the prosthesis. Thus, in these aspects, the translation distance can correspond to the thickness of the cartilage-like portion of the prosthesis. In some optional aspects, the thickness of the cartilage-like portion can be selected based on the thickness of cartilage for an average, healthy joint. Thus, for an osteochondral prosthesis, in some optional aspects, the first portion of the surface mesh can be translated away from the second surface by between 0.25 mm and 1.0 mm (e.g., optionally, about 0.5 mm), which corresponds to an exemplary range of cartilage thicknesses for healthy joints.

A first positive mold 130 can be formed from the first three-dimensional model 100 of the bone. For example, the first positive mold can be made via additive manufacturing (e.g., 3D printing) from a 3D model of the first positive mold. Likewise, a second positive mold 132 can be formed from the second three-dimensional model 122 of the bone, optionally, via additive manufacturing (e.g., 3D printing) from a 3D model of the second positive mold. Optionally, each of the first and second positive molds can comprise a polymer (e.g., acrylonitrile butadiene styrene). It is contemplated that the materials used to form the positive molds can be minimally reactive to the materials of the negative molds (e.g., polydimethylsiloxane (PDMS)) so that the positive and corresponding negative molds can be cleanly separated.

Figure 1B:
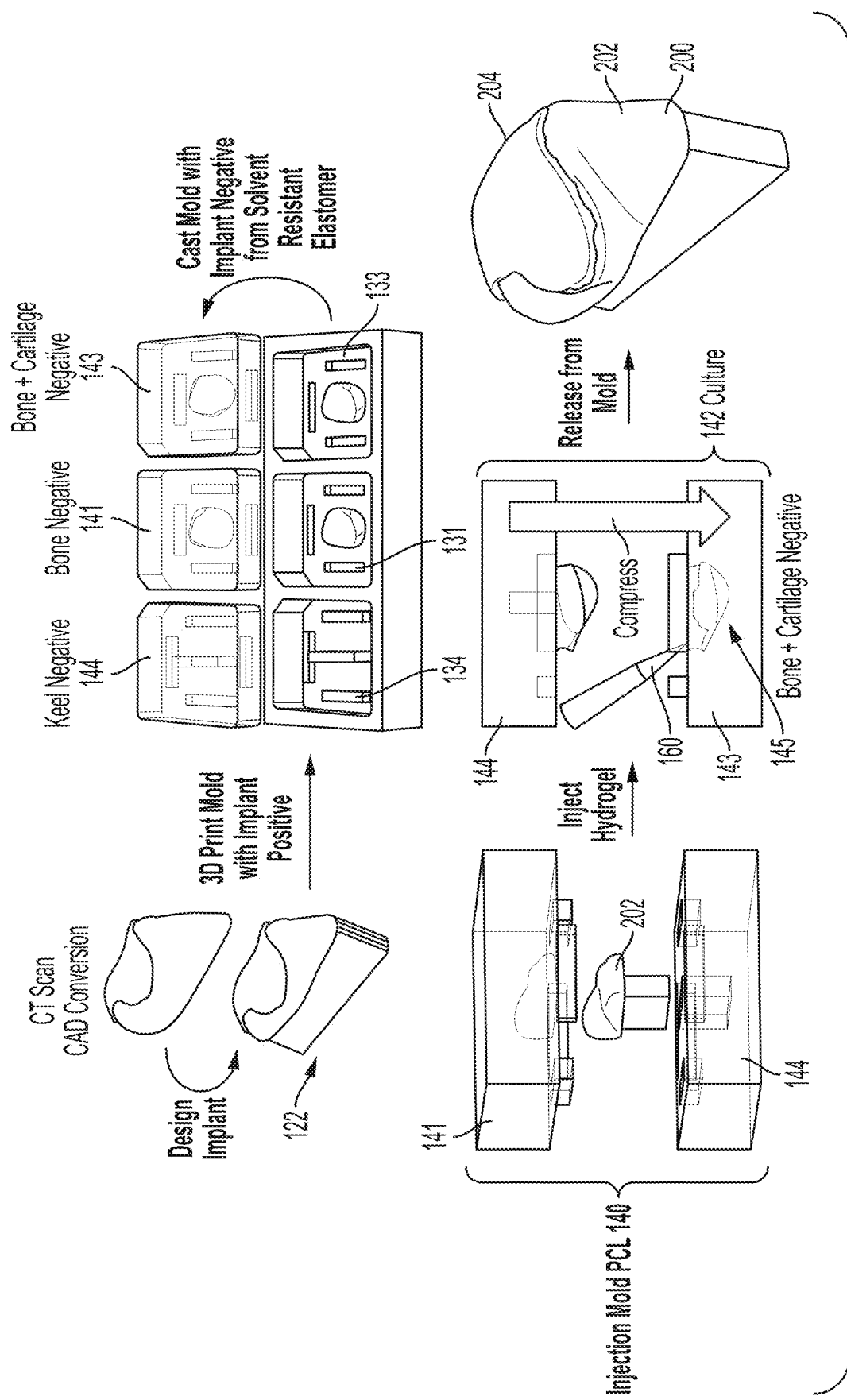
FIG. 1B is a flowchart with elements used in the method of making the prosthesis.
Figure 2:
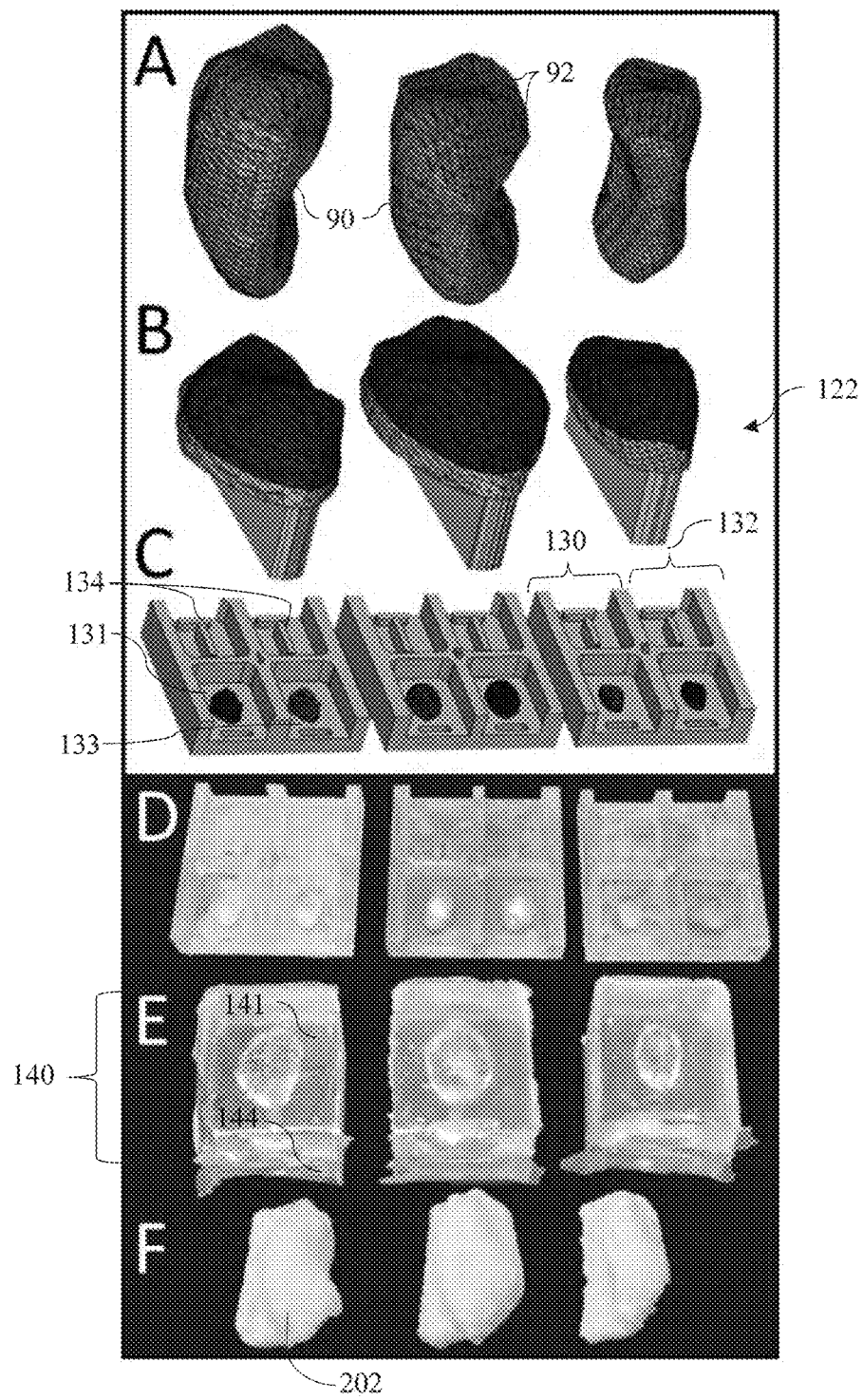
FIG. 2 shows exemplary elements produced at sequential steps of the method of making the prosthesis. Section A illustrates perspective views of medical images of bones. Section B illustrates three-dimensional meshes of prostheses. Section C illustrates a rendering of a three-dimensional (3D) file corresponding to a positive mold that can optionally be used to form a positive mold via 3D printing. Section D illustrates positive molds for forming the prostheses. Section E illustrates negative molds formed from the positive molds. Section F illustrates prostheses formed in the negative molds of Section E.
Figure 3:
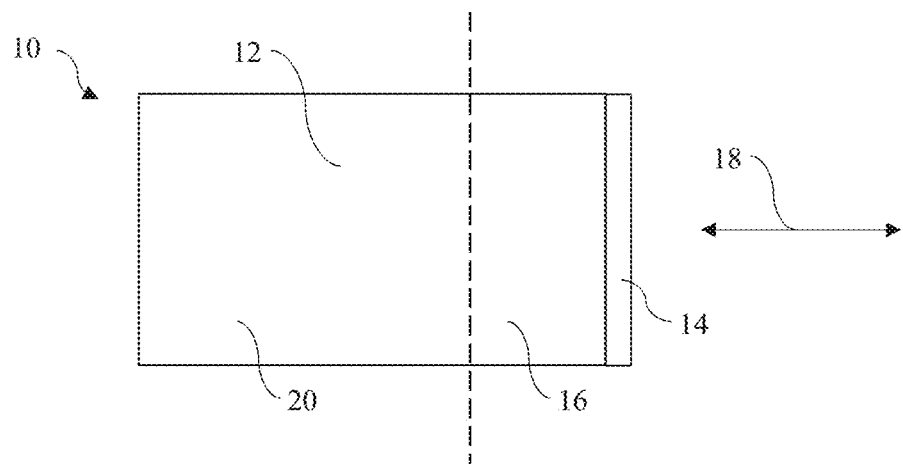
FIG. 3 is a schematic of a bone in accordance with embodiments disclosed herein.
Figures 4A, 4B:
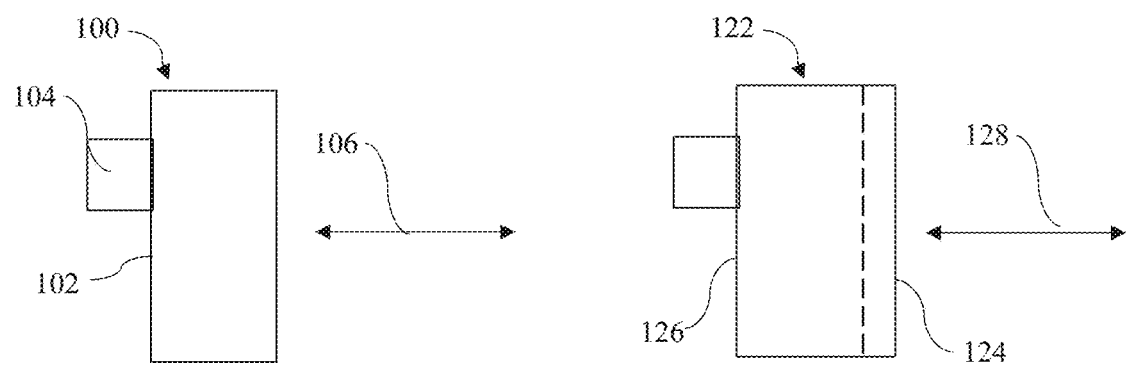
FIG. 4A is a schematic of a first three-dimensional model in accordance with embodiments disclosed herein.
FIG. 4B is a schematic of a second three-dimensional model in accordance with embodiments disclosed herein.
Figure 5A:
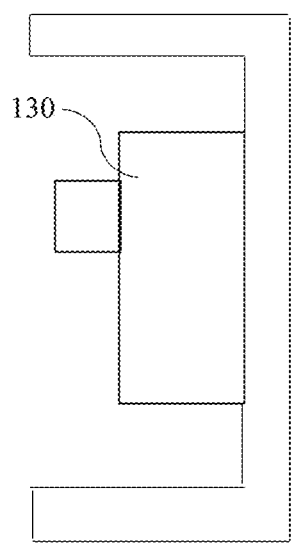
FIG. 5A is a schematic of a first positive mold formed from the first three-dimensional model of FIG. 4A.
Figure 5B:
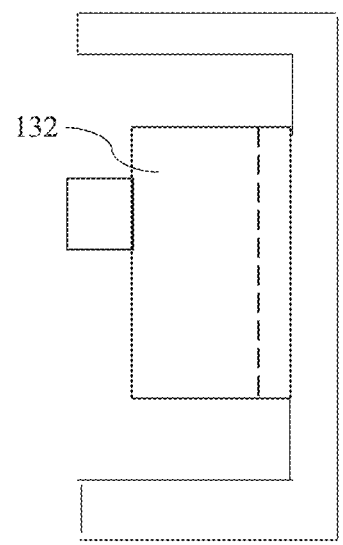
FIG. 5B is a schematic of a second positive mold formed from the second three-dimensional model of FIG. 4B.

In some optional aspects, the first positive mold 130 and second positive mold 132 can be integrally formed. Optionally, and as shown, the first positive mold 130 can comprise a first positive mold portion 131 and a third positive mold portion 134. Similarly, the second positive mold 132 can comprise a second positive mold portion 133 and a third positive mold portion 134. Optionally, as indicated in FIG. 1B, the same third positive mold portion 134 can be used to form both the first and second positive molds 130, 132. Moreover, the first positive mold 130 and second positive mold 132 can optionally share portions of the same unitary structure. In further aspects, as indicated in FIG. 2, the first and second positive molds 130, 132 can use separate third positive mold portions 134. In some optional aspects, the first positive mold 130 and second positive mold 132 can be formed as a single unitary structure.

In some optional aspects, the first and second positive mold portions 131, 133 can correspond to sections of the respective first and second three-dimensional models. For example, a first section of first three-dimensional model (e.g., the entirety of the first three-dimensional model excluding the keel) can define a shape of the first positive mold portion 131, and a second section of the first three-dimensional model (e.g., the keel) can define a shape of a third positive mold portion 134. Likewise, a first section of the second three-dimensional model (e.g., the entirety of the second three-dimensional model excluding the keel) can define a shape of the second positive mold portion 133.

Referring to FIGS. 1B, 2, and 8, a first negative mold 140 can be formed from the first positive mold 130. Likewise, a second negative mold 142 can be formed from the first positive mold 132. In some aspects, the first negative mold can comprise polydimethylsiloxane (PDMS). In optional aspects, the first negative mold can comprise Sylgard 184 prepared at a ratio of 10 parts monomer to 1 part curing agent. The negative mold can be cured, optionally at an elevated temperature (e.g., 40° C.).

It is contemplated that each of the first negative mold 140 and the second negative mold 140 can comprise a pair of mating components (that are configured to mate with or complementarily engage one another). For example, the first negative mold 140 can comprise a first negative mold portion 141 and a third negative mold portion 144. In some aspects, the third negative mold portion 144 can be formed from the third positive mold 134. The third negative mold 144 can cooperate with the first negative mold portion 141 to define the first negative mold 140 from which the bone-like portion 202 of the prosthesis 200 can be formed. Optionally, the first negative mold portion 141 can define a negative of a shape corresponding to the bone, and the third negative mold 144 can define the fixation element. Accordingly, in some aspects, the third negative mold 144 can define the fixation element, and the first negative mold portion 141 can define the remainder of the bone-like portion 202 of the prosthesis 200. The third negative mold 144 (optionally, the same third negative mold used to create the bone-like portion 202 or another third negative mold portion 144 formed from the third positive mold 134) can then cooperate with a second negative mold portion 143 to define the second negative mold 142. The second negative mold 142 can form the shape of the prosthesis 200, wherein the fixation element is received in the third negative mold portion 144, and the second negative mold portion 143 defines the remainder of the prosthesis (both the bone like portion 202, excluding the fixation element, and the cartilage-like portion 204).

The first and third negative mold portions 141, 144 can define one or more complementary alignment features 146. For example, the first negative mold portion 141 can define a cylindrical protrusion 148 and a rectangular protrusion 150, and the third negative mold portion 144 can define a matching cylindrical bore 152 and rectangular bore 154 that can receive the cylindrical protrusion 148 and rectangular protrusion 150, respectively. More generally, it is contemplated that the first negative mold portion 141 can define at least one protrusion that is configured for receipt within a corresponding bore of the third negative mold portion 144. In this way, the first and third negative mold portions 141, 144 can be aligned. It is contemplated that the second and third negative mold portions 143, 144 can likewise comprise the same or similar complementary alignment features.

The bone-like portion 202 of the prosthesis 200 can be formed within the first mold. For example, a mixture comprising poly(ε-caprolactone) (PCL) dissolved in a solvent (optionally, in chloroform at 20% wt/vol) can be provided into the first mold to produce a PCL-based foam. In some aspects, the negative mold can comprise an inlet 147 (FIG. 8) that can receive the mixture into the interior of the negative mold. It is further contemplated that, in some optional aspects, the inlet 147 can define a surface of the negative mold that forms at least a portion of the fixation element 104. It is further contemplated that the solvent can comprise tetrahydrofuran (THF) or Dimethylformamide (DMF), chloroform, or a combination thereof. In some optional aspects, the mixture can further comprise sodium chloride crystals. In optional aspects, the salt crystals can each have major dimensions between 100 and 300 microns. Optionally, it is contemplated that the salt crystals can be passed through both an upper limit sieve and a lower limit sieve to select the salt crystals within the desired size range. In still further optional aspects, the mixture can comprise hydroxyapatite or another suitable bone-promoting factor. Optionally, zirconium nanoparticles can be included for radioopacity at a density of 3%. The radioopacity can be beneficial for assessing placement of the prosthesis. The use of PDMS as a negative mold material can be beneficial because, unlike most thermoplastics (particularly those used for 3D printing), the PDMS is resistant to the chloroform used in the PCL slurry. PDMS is also gas-permeable, allowing the solvent to quickly evaporate from the mold, leaving the solid construct.

In aspects in which the mixture comprises sodium chloride crystals, once the solvent has evaporated, the bone-like portion can be soaked in water (or other suitable solvent) to dissolve the sodium chloride crystals, thereby providing a porous structure. Thus, it is contemplated that the size and distribution of salt crystals can be selected or modified to produce pores of desired sizes and at desired locations. The pores can promote ingrowth and integration as well as provide conduits for nutrient transport.

The cartilage-like portion can then be formed on the bone-like portion. For example, the bone-like portion can be positioned within the second negative mold. Optionally, the second negative mold 142 can be identical to the first mold except for the translated surface that defines space 145 (FIG. 1B) for forming the cartilage-like portion on the prosthesis. The bone-like portion can be in a select position so that the second mold and bony portion cooperate to define a cartilage space (i.e., a volume that is desired to form the cartilage-like portion). The same third mold or a copy of the third mold can cooperate with the second mold to define a space in which the bone-like portion is received. The cartilage space can be filled with a material 160 to form the cartilage-like portion of the prosthesis. In some aspects, the cartilage space can be filled with the material for forming the cartilage-like portion, and then the bone-like portion can be placed in the second negative mold. It is contemplated that the bone-like portion can at least partially displace the material for forming the cartilage-like portion when the bone-like portion is inserted into the second negative mold.

The material for forming the cartilage-like portion can comprise a hydrogel. In some optional aspects, they hydrogel can comprise methacrylated hyaluronic acid (meHA). In further aspects, methacrylated gelatin, agarose, alginate, collagen, or other suitable material can be used. For acellular constructs, polyethylene glycol diacrylate or PEGDA can achieve the mechanical properties of native cartilage. These hydrogels can also be modified with additional chemical groups to improve cell-material interaction. Growth factor eluding materials could also be encapsulated in the gel to improve tissue maturation.

The material for forming the cartilage-like portion can further comprise a photoinitiator. In optional aspects, the material can further comprise stem cells. In some aspects, the material can comprise between 10 million and 100 million stem cells per milliliter. Optionally, the stem cells can comprise mesenchymal stem cells (MSCs) or similar cells that can be from an autologous source (e.g., isolated from marrow or chondrocytes of the patient). In further embodiments, stem cells can comprise bovine MSCs. In further aspects, the stem cells can comprise adipose derived stem cells, induced pluripotent stem cells, or stem cells derived from any other source.

The hydrogel can be cross-linked via light-mediated cross-linking. It is contemplated that light-mediated cross-linking can allow the cross-linking to occur on-demand, thereby providing flexibility in working with the hydrogel (e.g., mixing stem cells, etc.) prior to the hydrogel setting. In some aspects, the light source used for cross-linking can depend on the photoinitiator used. For example, a visible or ultraviolet (UV) light source can be used to cross-link the hydrogel. It is further contemplated that the second negative mold can comprise a material that is optically transparent, or substantially optically transparent, for the electromagnetic spectrum used in cross-linking (e.g., visible or UV light). For example, in some optional aspects, the second mold can comprise PDMS (e.g., using the preparation of Sylgard 184 as disclosed herein). In alternative optional aspects, the hydrogel can be cross-linked via thermosetting or chemically mediated crosslinking.

There are significant limitations on the types of materials that can be used with conventional negative molds. First, conventional molds are opaque, eliminating the ability to photocrosslink polymers in a complex geometry. Second, conventional molds are made from materials that are sensitive to chemical erosion, making them incompatible for the PCL foam fabrication process described herein. In contrast, the disclosed negative mold(s) can be optically clear, thereby enabling photocrosslinking of polymers in a complex geometry. Further, the disclosed negative mold(s) can be chemically resistant, thereby enabling molding of PCL foam as disclosed herein.

The prosthesis can be precultured in vitro or directly implanted to replace an osteochondral tissue.

To implant the prosthesis, it is contemplated that a portion of the original bone can be removed using surgical tools. The prosthesis can be inserted into the bone until the prosthesis interface engages a cut portion of the bone. One or more (optionally, a plurality of) fixation elements 210 (e.g., optionally, screws, pegs, and/or sutures) can then fix the prosthesis to the bone, and any surgical wounds can be closed. Bone ingrowth and integration between the bone and the prosthesis can occur over time.

EXAMPLES

The following examples demonstrate efficacy of the methods disclosed herein.

Example 1

Eight AC bones were isolated from the right forelimbs of adult Yucatan minipigs and four human trapezia were isolated from cadaveric donors. Samples were fixed in formalin and imaged via μCT (VivaCT 75, Scanco), before and after immersion in Lugol's solution (5% I2, 10% KI in water) to enhance cartilage contrast. DICOMs from the initial scan were imported into ITK-SNAP and bone segmented. A surface mesh was exported to Meshlab (ISTI) for simplification and Solidworks (Dassault Systèmes) to render 3D objects and compute bone volume and surface features. Post-Lugol's scans were manually registered with the bone and processed similarly, with the cartilage layer segmented in a semi-automated manner. After imaging, samples were decalcified, processed into paraffin, sectioned, and stained with Safranin-O/fast green to visualize cartilage, bone, and fibrous tissue and Picrosirius red, to visualize collagen. Immunohistochemistry was used to assess distribution of collagen II. In Solidworks, an implant of the articulating cartilage surface and first third of the AC bone was designed. A cylindrical peg was included for fixation into the parent bone. Negative molds were designed for both the bone portion and the composite implant. The bone mold was 3D printed out of aluminum alloy using direct metal laser sintering (DMLS), and the composite mold was 3D printed in an ABS-like photopolymer. To form the bone-like portion of the prosthesis, poly(ε-caprolactone) (PCL) was dissolved in chloroform at 20% wt/vol and mixed with NaCl crystals sieved to ~106 μm with inclusion of Zirconium nanoparticles for radioopacity. The slurry was poured into the bone mold and the solvent was evaporated for 5 days. The units were demolded and washed in distilled water to remove salt. The resultant construct was imaged via μCT (μCT50, Scanco medical). As a proof of concept, a 5 wt % agarose solution doped with red food coloring for visualization was poured into the composite mold, and the PCL bone-like portion of the prosthesis was added to shape the cartilage portion. Finally, a 1% wt/vol methacrylated hyaluronic acid (MeHA) solution with 20 million juvenile bovine mesenchymal stem cells (MSCs) per mL was dispensed into the composite mold and the porous bone component placed into the mold to form the final shape of the cartilage. Gelation occurred via inclusion of APS/TEMED, with entire mold placed at 37° C. for 10 minutes. After 24 hours in culture, construct viability was assessed.

Figure 7:
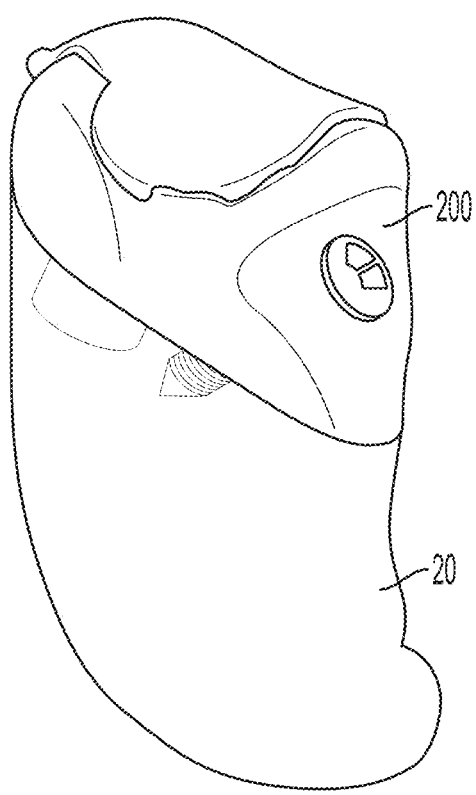
FIG. 7 is a perspective view of the prosthesis of FIG. 6.
Figure 9:
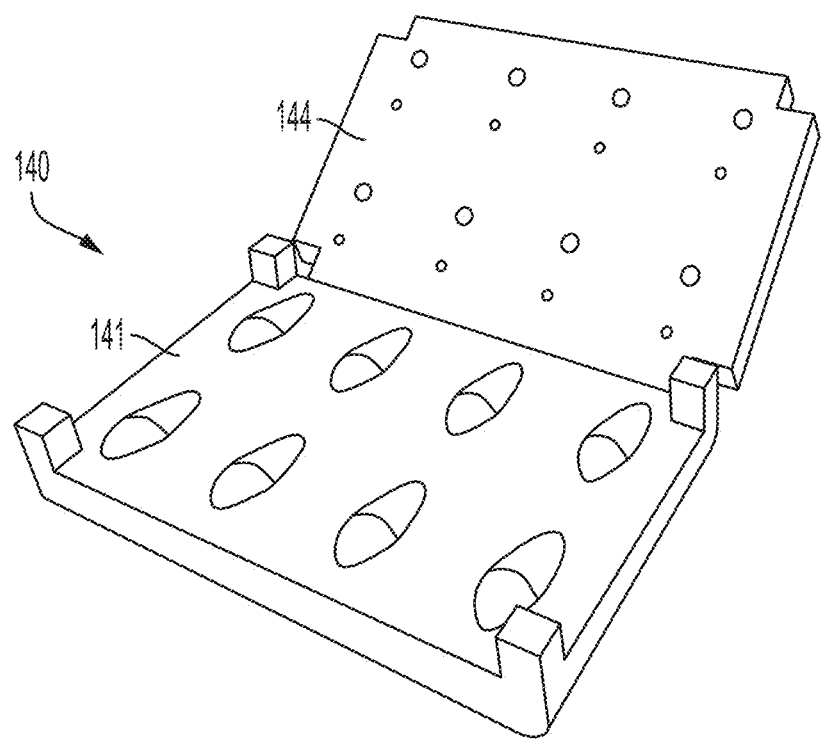
FIG. 9 is a perspective view of a negative mold for forming (optionally, simultaneously forming) a plurality of prostheses.
Figure 10:
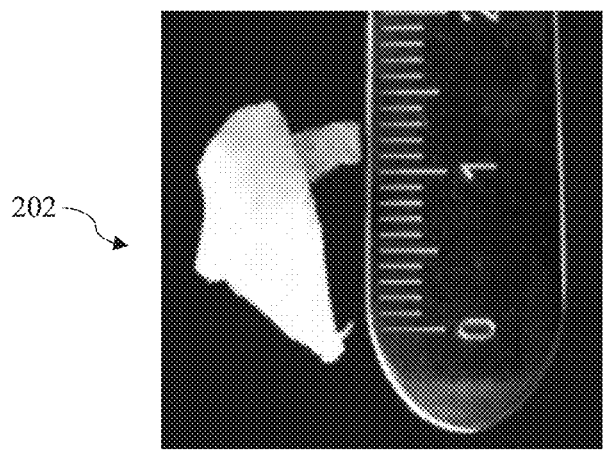
FIG. 10 is a perspective view of a bone-like portion of the prosthesis.
Figure 11:
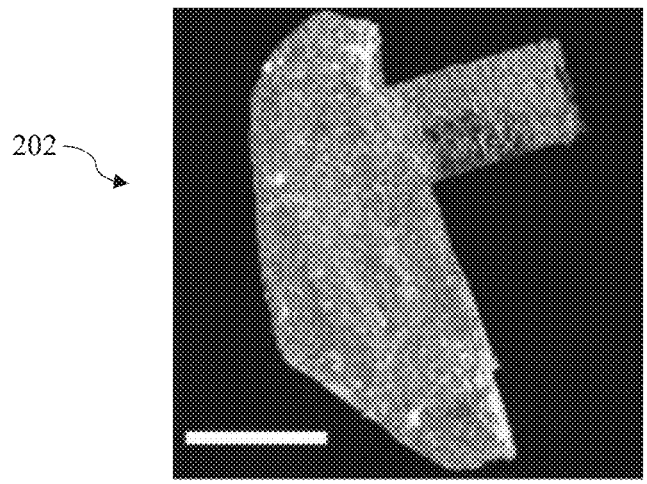
FIG. 11 is a microCT scan of the bone-like portion of FIG. 10.
Figure 12:
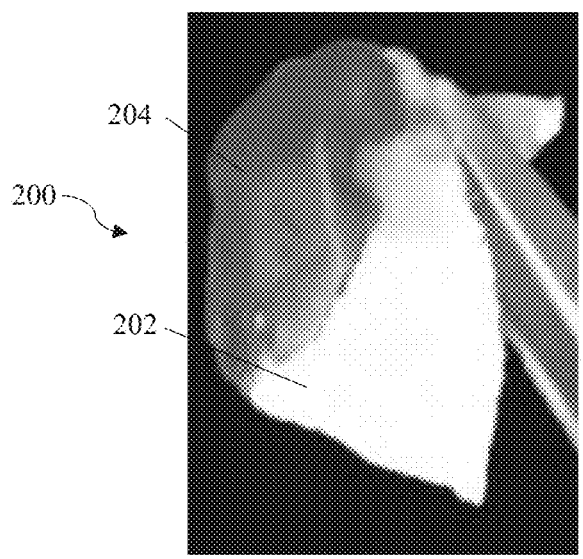
FIG. 12 is a perspective view of the prosthesis, comprising the bone-like portion and a cartilage-like portion.
Figure 13:
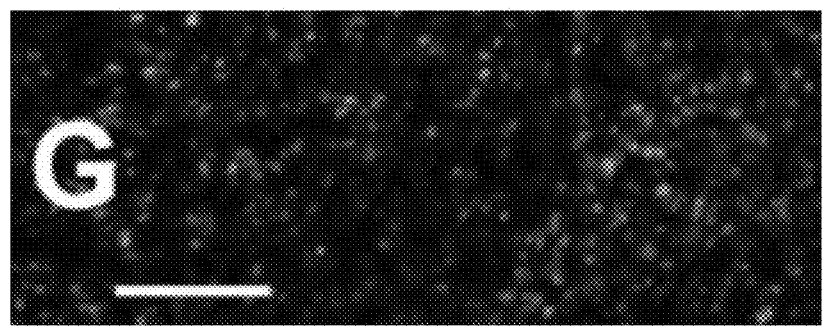
FIG. 13 is an image showing live stem cells in the cartilage-like portion of the prosthesis.
Figure 14:
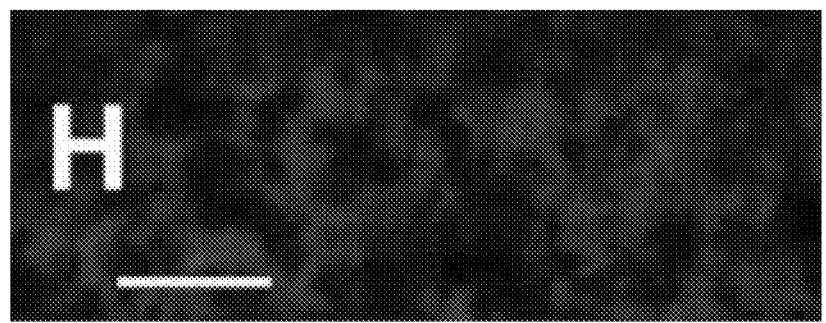
FIG. 14 is a confocal image showing the formation structure of the bone-like portion of the prosthesis.

Results: The porcine AC bone shows marked anatomical similarity to the human trapezium in both its size and saddle shape of its major articulating surface. Both species show strong staining for proteoglycans on their cartilage surfaces, and collagen throughout the tissue depth. Type II collagen is high in the cartilage surface of both the human trapezium and porcine AC. Using surface meshes generated from μCT, an implant was designed to replace the full articulating surface of the porcine AC. (FIGS. 6-7) The boney portion of this implant was generated using PCL foam (FIGS. 8-10). MicroCT showed that this recapitulated the geometry of the original design yielding a volume that was 76% similar to the template (FIG. 11). A second mold with both the bone-mimicking and cartilage portion of the implant formed a combined implant (FIG. 12). When cast into this composite, MSCs remained viable (FIG. 13, showing areas with live MSCs as light with a scale of 200 μm). FIG. 14 illustrates a confocal image of the porous PCL structure with a scale of 200 microns.

Example 2

Assessment of the AC: Eight AC bones were isolated from the right forelimbs of adult Yucatan minipigs, and four human trapezia were isolated from cadaveric donors. A custom indentation testing setup was used to evaluate cartilage mechanics of the AC via stress relaxation tests. The saddle-shaped articular cartilage surface was indented with a 2 mm diameter spherical indenter in three locations (superior, middle, and inferior). Four compressive ramps (10% strain each) were applied, with a 600 s relaxation between each step. The equilibrium modulus was calculated from the second step. Human and porcine samples were fixed and imaged via μCT (VivaCT 75, Scanco), before immersion in Lugol's solution (5% I2 10% KI in water) to enhance cartilage contrast. DICOMs from the initial scan were imported into ITK-SNAP5 and bone was segmented. A surface mesh was exported to Meshlab (ISTI) for simplification. Post-Lugol's scans were manually registered with the bone and processed similarly, with the cartilage layer segmented in a semi-automated manner. Samples were analyzed histologically with Safranin-O/fast green to visualize cartilage, bone, and fibrous tissue.

Figure 15:
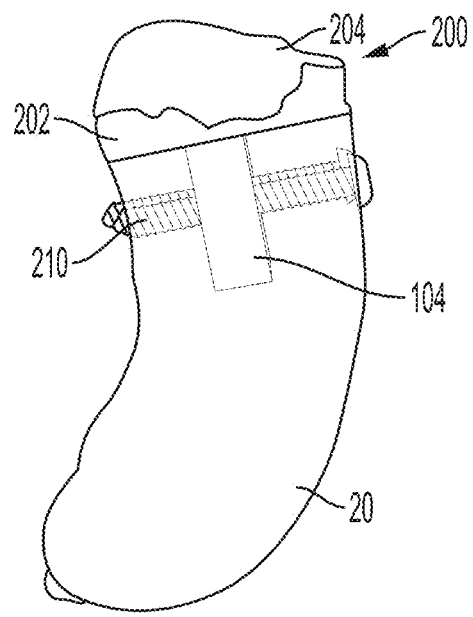
FIG. 15 is front view of an exemplary prosthesis in accordance with the present disclosure implanted in a bone.
Figure 16:
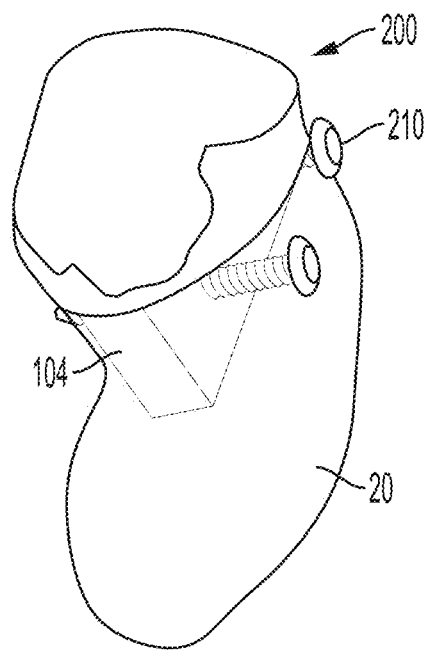
FIG. 16 is a perspective view of the prosthesis of FIG. 15.
Figure 17:
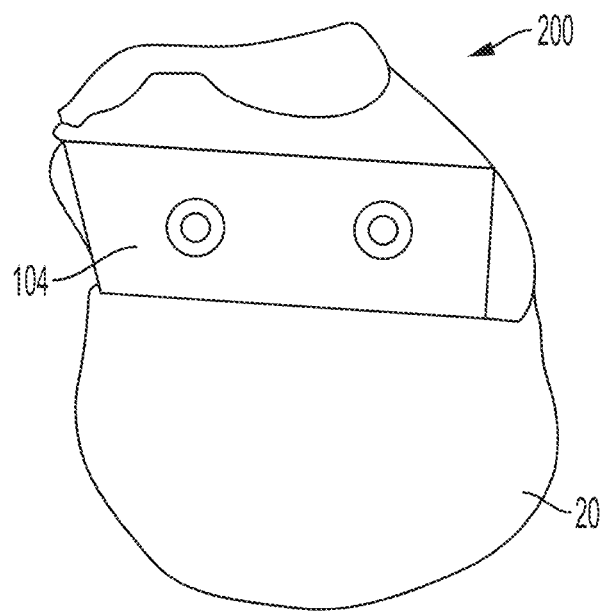
FIG. 17 is a front view of the prosthesis of FIG. 15.
Figure 18:
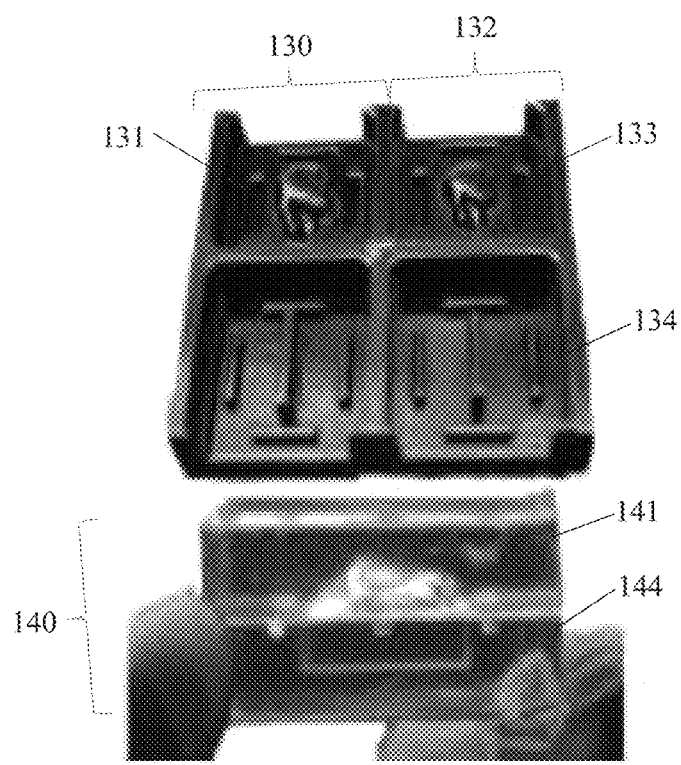
FIG. 18 is a perspective view of a positive mold and a side view of a negative mold in accordance with embodiments disclosed herein.

AC Contact Mechanics: CT images of the forelimb of skeletally mature Yucatan minipigs were obtained and 3D models of the bones were generated. A musculoskeletal model was generated in OpenSim, and the relative motion of the AC and its contact forces was evaluated through a passive range of motion. In 3 additional minipig forelimbs, a TekScan iScan 6900 pressure sensor was inserted between the accessory carpal and the ulnar carpal. The carpus was moved through a range of angles from 90 degrees to full extension, while contact forces were measured. Development of AC Replacements: In Solidworks, an implant of the articulating cartilage surface and first third of the AC bone was designed using the μCT data (FIGS. 15-17). A 2 mm thick by 5 mm deep "keel" was added for fixation. Positive molds were 3D printed out of an ABS-like photopolymer (FIG. 18). To fabricate elastomeric negative molds, Sylgard 184 (polydimethylsiloxane, PDMS) was poured over the 3D printed designs, degassed, and allowed to cure at 40° C. overnight. To fabricate porous anatomical implants, poly(ε-caprolactone) (PCL) was dissolved in chloroform at 20% wt/vol and mixed with NaCl crystals sieved to ~106 μm. Zirconium nanoparticles were included for radioopacity. The slurry was poured into the mold and the solvent was evaporated. The units were demolded and the salt was leached. Implantation of Engineered AC: Next, a proof-of-concept implantation in an adult minipig was performed. The carpus was exposed and rotated so that the articulating surface of the AC was in view. A reciprocating saw and osteotome were used to remove the surface of the AC and a 2 mm burr was used to create a slot in the remaining bone, matching the keel on the implant. The construct was fixed in place with two 1 mm Ø by 8 mm bicortical screws oriented normally to the plane of the keel. Fluoroscopy confirmed implant positioning. After 1 week, the animal was sacrificed and the implant was retrieved and evaluated by μCT.

Results: The porcine AC bone shows marked anatomical similarity to the human trapezium in both its size and saddle shape of its major articulating surface. Both showed strong staining for proteoglycans on their cartilage surfaces and fibrous tissue at their peripheries. The average thickness of the AC articular cartilage ranged from 350-500 μm within the contour of the main articulating surface (FIG. 21A). The equilibrium modulus in the superior, middle, and inferior regions was 0.93+/−0.54, 1.40+/−0.67, and 1.36+/−0.60 MPa, respectively. In the OpenSim model, contact force remained ~0N as the carpus was extended, until ~20° flexion. After this point, force increased and reached a peak of 67N at full extension (FIG. 21C). In the ex vivo experiment (FIG. 22D), contact area across the joint remained close to 0 mm2 until 15° of flexion, and then rose rapidly as the angle approached 0° (FIG. 22E). Force (FIG. 22F) followed the same pattern, reaching its maximum of 29.1±10.5N at 0°.

Using anatomic renderings generated from μCT, an implant was designed to replace the articular surface of the porcine AC.

Using a 3D printed positive mold, a PDMS negative mold was produced (FIG. 18) which was used to create a porous PCL implant (FIG. 19). This was implanted into a living pig (FIGS. 20A-20C), which began weight bearing soon after surgery (FIGS. 20A-20G). The implant remained intact and in place after 1 week. (FIGS. 20E-20G).

Example 3

Figure 22B:
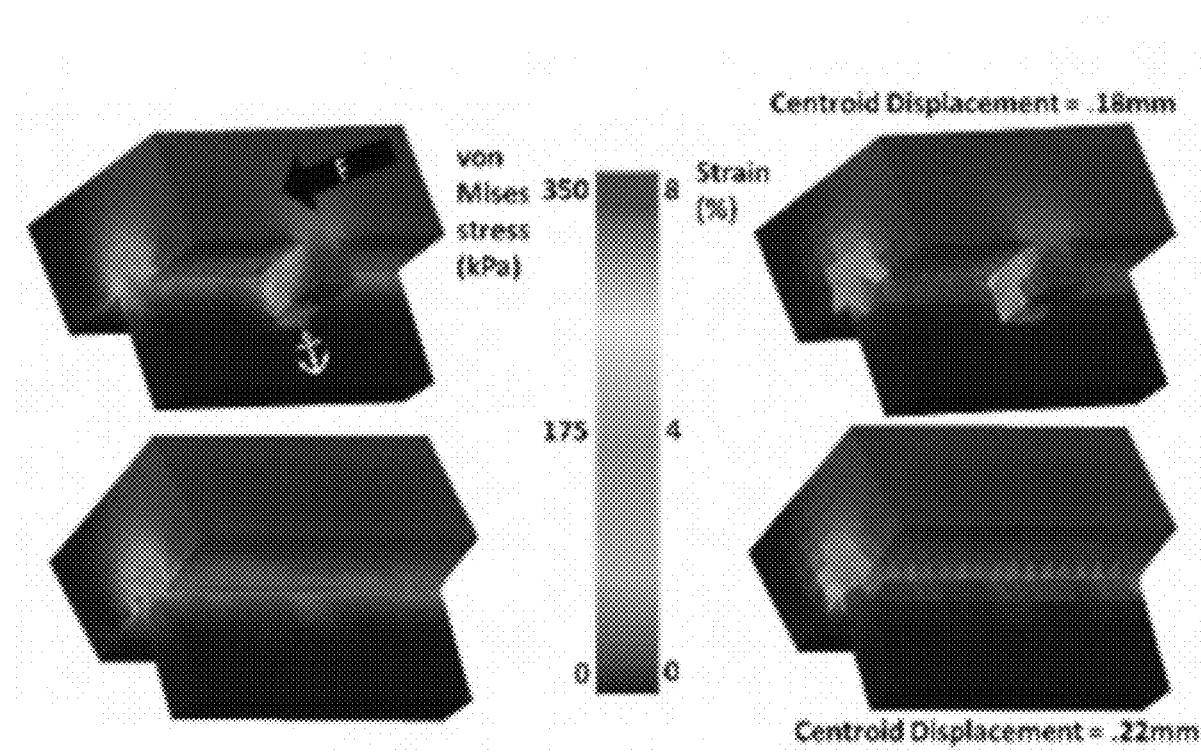
FIG. 22B illustrates stress simulations on the keel structures of FIG. 22A.

CT images of the forelimb of a skeletally mature Yucatan minipig were obtained and 3D models of the bones were segmented in ITK-SNAP7. A musculoskeletal model was generated in OpenSim, and the relative motion of the AC and its contact forces were evaluated through passive range of motion. Three adult minipig forelimbs were obtained from unrelated studies. In each, an incision was made and a TekScan iScan 6900 pressure sensor was placed into joint space between the accessory carpal and the ulnar carpal. The carpus was moved through a range of angles from 90 degrees to full extension while contact forces were measured. To reduce the bone-like portion of the implant while simultaneously increasing surface area for potential cell ingress and boney integration, our previous implant was redesigned. Two different surgical fixation designs were evaluated—a "cross" keel and a single "keel" design (FIG. 22A). Simplified mock-ups of the cross keel and single keel fixation methods were created in Solidworks (Dassault Systèmes), and a finite element analysis was performed (FIG. 22B). The keel was rigidly fixated and a 3N load was applied to the lateral face of the implant, with the materials assigned a bulk modulus of 3 MPa. Positive molds of the keel design were 3D printed out of an ABS-like photopolymer. To fabricate elastomeric negative molds, Sylgard 184 (polydimethylsiloxane, PDMS) was prepared at a 10 parts monomer to 1 part curing agent ratio, poured over the 3D printed designs, degassed, and allowed to cure at 40° C. overnight. Poly(ε-caprolactone) (PCL) was dissolved in chloroform at 20% wt/vol and mixed with NaCl crystals sieved to ~106 μm, and Zirconium nanoparticles were included for radioopacity. The slurry was poured into the mold and the solvent was evaporated. The units were demolded and the salt was leached. We next performed a proof-of-concept surgery on an adult minipig forelimb. We made an incision into the joint and rotated the articulating surface of the AC into view. We used a reciprocating saw followed by an osteotome to remove the surface of the AC and a 2 mm burr followed by a curette to create a slot in the remaining bone, matching the keel on the implant. The construct was held in place with two 1 mm Ø by 8 mm long bicortical screws oriented normally to the plane of the keel. Fluoroscopy and MicroCT was performed to evaluate positioning of the implant. Images were segmented using ITK-SNAP and visualized in Meshlab (ISTI).

Results: In the OpenSim model, the contact force remained —0 as the carpus was extended until ~20 degrees flexion. At this point, force increased and reached a peak of 67N at full extension (FIG. 21C). In the ex vivo experiment (FIG. 21D), the force across the joint remained close to zero until 15 degrees of flexion, and then rose rapidly to a maximum of 29.1±10.5N at 0 degrees (FIG. 21E). The contact area and stress followed the same pattern. The AC implant design from our previous work had a volume of 423 $mm^3$ and an integrating surface area of 129.3 $mm^2$. Two new designs—the cross keel and single keel, had volumes of 380.75 $mm^3$ and 355.65 $mm^3$ and integrating surface areas of 240.5 $mm^2$- and 215.6 $mm^2$, respectively (FIG. 22A). FE modeling showed that the centroid of the implant displaced by 0.18 mm in the cross keel design and 0.22 mm in the single keel design (FIG. 22B). Neither experienced local strains over 7%. We chose the single keel design for implantation. Using a 3D printed positive mold, we produced a PDMS negative mold which was used to create a porous PCL implant. This was readily implanted into a cadaveric minipig forelimb and was visible fluoroscopically and on μCT.

Example 4

Construct Design and Fabrication: Clinical CT images of three forelimbs of skeletally mature Yucatan minipigs were obtained with a portable 8-slice CT scanner (CereTom, Neurologica). From these, the AC bones were segmented using ITK-SNAP7. For each, a surface mesh was exported and opened in MeshLab (ISTI), where the mesh was smoothed and simplified. This mesh was imported into Solidworks (Dassault Systémes) and a 3D object was created. The articulating surface was translated normally 500 μm and the resulting shell became the "cartilage" of the implant. Next, a plane was defined parallel to and ~3 mm deep from the top of the bone; this plane was used to remove the bottom portion. Finally, a 2 mm wide by 5 mm deep "keel" was added to the bottom of the bone to enable subsequent fixation. A positive mold of both the bone only and composite implant was then designed and 3D printed. To fabricate elastomeric negative molds, Sylgard 184 (polydimethylsiloxane, PDMS) was prepared at a 10 parts monomer to 1 part curing agent ratio, poured over the 3D printed designs, degassed, and allowed to cure at 40° C. overnight. Poly(ε-caprolactone) (PCL) was dissolved in chloroform at 20% wt/vol and mixed with NaCl crystals sieved to ~106 μm with inclusion of Zirconium nanoparticles for radio-opacity. The slurry was poured into the mold and the solvent was evaporated. The units were demolded and the salt was leached. A 30% solution of poly(ethylene glycol) diacrylate (PEGDA) containing 0.05% Lithium phenyl-2,4,6-trimethylbenzoylphosphinate (LAP) photoinitiator was added to the bone and cartilage composite mold, the PCL "bone" portion was added, and the hydrogel was polymerized using UV light at 380 nm for 10 minutes to form a 'cartilage' cap on the implant. Geometry measurement: The thickness of the designed cartilage surface of each implant was measured in Solidworks on a grid spacing of 1.25 mm and compared with previously generated thickness maps based on native AC cartilage. Each of the three animal-specific implants was scanned via μCT (μCT50, Scanco medical), and the results were segmented, cleaned, and imported into Solidworks and compared to the original designs. Joint Biomechanics: In each of the three forelimbs, an incision was made and a TekScan iScan 6900 pressure sensor was inserted into the joint space between the AC and the ulnar carpal. The carpus was extended through a range of angles from 90 degrees to 0° while contact forces were measured. Next, composite AC constructs were implanted. A reciprocating saw was used to remove the surface of the AC and a 2 mm burr to create a slot in the remaining bone matching the keel on the construct. After implantation, TekScan measurements were repeated. T-tests at 0° compared force and contact area pre- and post-op, with $p<0.05$ indicating significance.

Figure 23A:
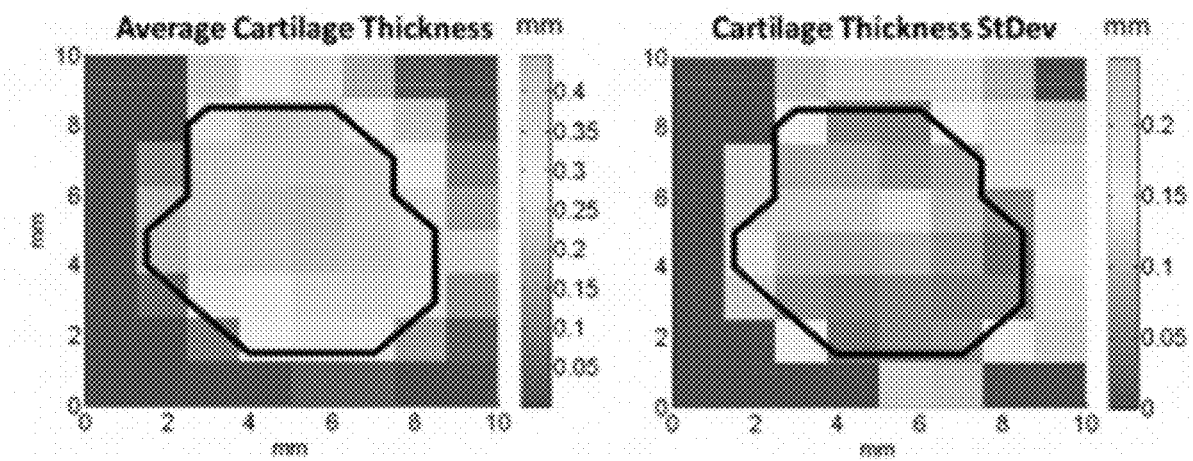
FIG. 23A illustrates cartilage thickness measurements of an ex vivo connective tissue sample of a test subject.
Figure 23B:
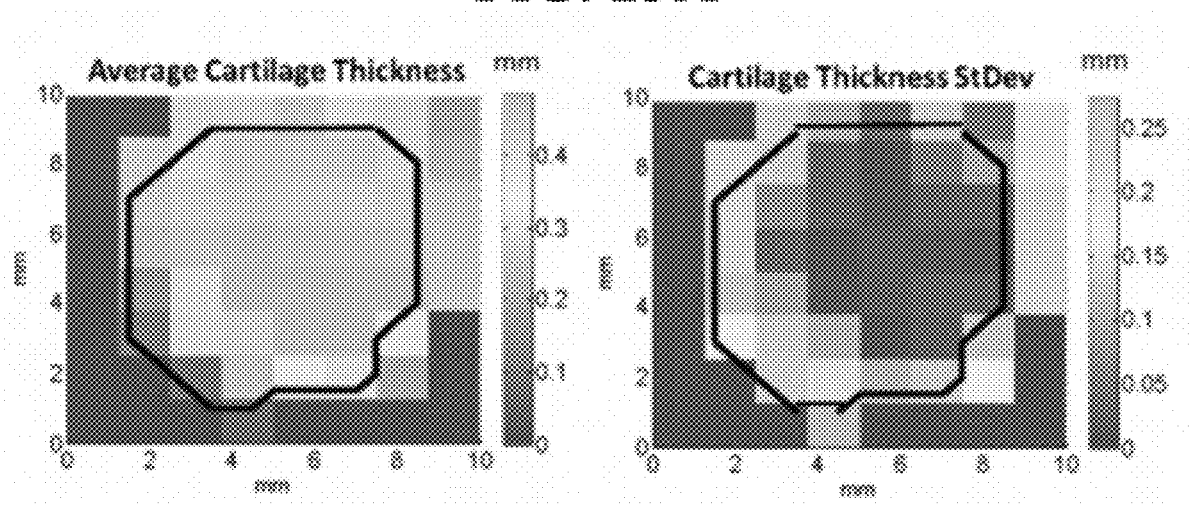
FIG. 23B illustrates thickness measurements of a cartilage-like portion of an exemplary test prosthesis.
Figure 23C:
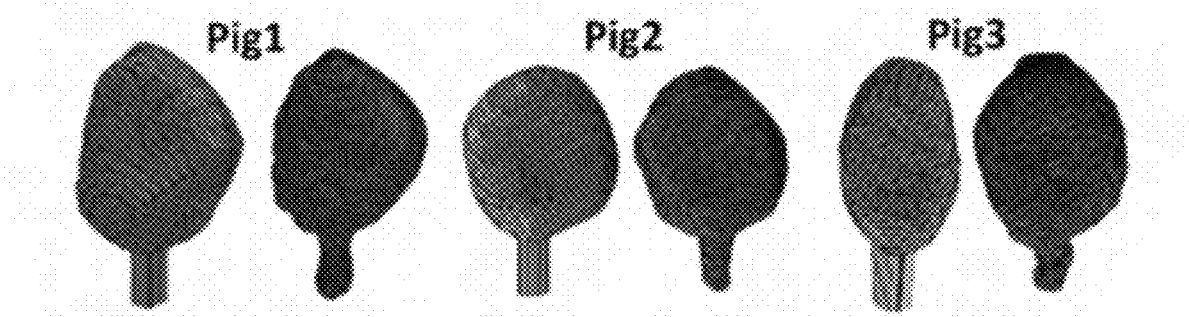
FIG. 23C illustrates three design (left) and fabricated PCL implants as determined from μCT imaging (right) of each of the three individuals.

Results: Starting from clinical CT, we designed animal-specific implants to replace the surface of the AC and molds with which to fabricate them (FIG. 2). Our design technique resulted in a cartilage thickness of ~400-500 μm throughout, much like the native tissue (FIGS. 23A-23B). Scanning the fabricated constructs by μCT showed that they faithfully reproduced the designs. In the joint loading experiments (FIGS. 24A-F), in all preoperative trials, as the limb was extended from 90° to full extension, force and contact area remained close to 0N until the joint approached 0° at which point the average force rose to 21.6N and the average contact area rose to 74.2 mm². Post-implantation, a similar loading pattern was observed, with force averaging 21.5N and contact area averaging 72.0 mm².

Computing System

Figure 25:
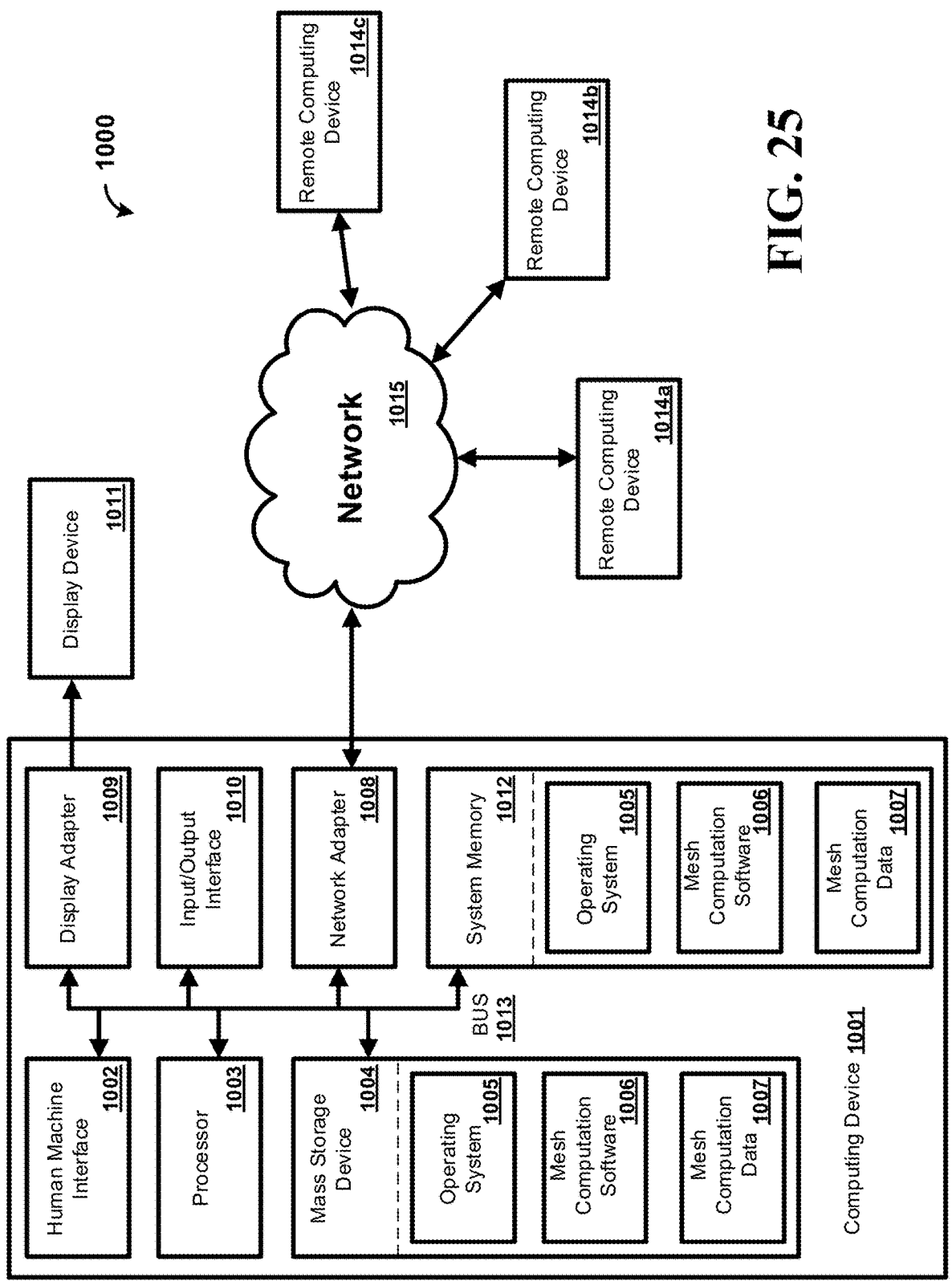
FIG. 25 illustrates a computing system for use in various aspects of the methods for forming prostheses as disclosed herein.

FIG. 25 shows an exemplary computing system 1000 that can be used to for various aspects of the disclosed methods. For example, a computing device of the computing system can be used to generate and manipulate the 3D models (e.g., surface meshes). It is contemplated that a display of the computing device can permit viewing and observation of the 3D models disclosed herein. The same or another computing device of the computing system can execute instructions for controlling a 3D printer for forming a mold (e.g., a positive mold or a negative mold), as disclosed herein. Optionally, it is contemplated that one or more of the computing devices of the system can be communicatively coupled to an imaging device and/or database that receives images of at least a portion of a bone as further disclosed herein.

Computing system 1000 can include a computing device 1001 and a display 1011 in electronic communication with the computing device, which can be any conventional computing device, such as, for example and without limitation, a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. In some optional embodiments, a smart phone, tablet, or computer (i.e., a laptop or desktop computer) can comprise both the computing device 1001 and the display 1011. Alternatively, it is contemplated that the display 1011 can be provided as a separate component from the computing device 1001. For example, it is contemplated that the display 1011 can be in wireless communication with the computing device 1001, thereby allowing usage of the display 1011 in a manner consistent with that of the display of a remote device as disclosed herein.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as mesh computation data 1007 and/or program modules such as operating system 1005 and mesh computation software 1006 that are accessible to and/or are operated on by the one or more processors 1003.

The computing device 1001 may also comprise other removable/non-removable, volatile/non-volatile computer storage media. A mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and the mesh computation software 1006 may be stored on the mass storage device 1004. One or more of the operating system 1005 and the mesh computation software 1006 (or some combination thereof) may comprise program modules. Mesh computation data 1007 may also be stored on the mass storage device 1004. The mesh computation data 1007 may be stored in any of one or more databases known in the art. The databases may be centralized or distributed across multiple locations within the network 1015.

A user may enter commands and information into the computing device 1001 via an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 1003 via a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display 1011 may also be connected to the bus 1013 via an interface, such as a display adapter 1009. It is contemplated that the computing device 1001 may have more than one display adapter 1009 and the computing device 1001 may have more than one display 1011. A display 1011 may be a monitor, an LCD (Liquid Crystal Display), light emitting diode (LED) display, television, smart lens, smart glass, and/or a projector. In addition to the display 1011, other output peripheral devices may comprise components such as speakers (not shown) and a printer (not shown) which may be connected to the computing device 1001 via Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014a,b,c. A remote computing device 1014a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014a,b,c may be made via a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. In further exemplary aspects, it is contemplated that the computing device 1001 can be in communication with the remote computing devices 1014a,b,c through a Cloud-based network.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of the mesh computation software 1006 may be stored on or sent across some form of computer readable media. Any of the disclosed methods may be performed by processor-executable instructions embodied on computer readable media.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A method for forming a prosthesis having a bone-like portion and a cartilage-like portion, the method comprising: additively manufacturing a first positive mold in accordance with at least a portion of a first three-dimensional model of at least a portion of a bone; forming a first negative mold from the first positive mold; creating the bone-like portion of the prosthesis within the first negative mold; additively manufacturing a second positive mold of the bone and a cartilage from a second three-dimensional model, wherein a portion of the second three-dimensional model corresponds to a portion of the first three-dimensional model; forming a second negative mold from the second positive mold; positioning the bone-like portion of the prosthesis in the second negative mold so that the second negative mold and bone-like portion of the prosthesis define a cartilage space; and filling the cartilage space with a material to form the cartilage-like portion of the prosthesis.

Aspect 2: The method of aspect 1, wherein forming the negative mold from the first positive mold comprises forming the first negative mold from polydimethylsiloxane (PDMS).

Aspect 3: The method of aspect 1 or aspect 2, wherein creating the bone-like portion comprises filling the first negative mold with a mixture comprising polycaprolactone (PCL) dissolved in chloroform and allowing the chloroform to evaporate from the mixture.

Aspect 4: The method of aspects 1-3 wherein the bone-like portion contains a bone-promoting factor Aspect 5: The method of aspect 3 or aspect 4, wherein the mixture further comprises sodium chloride crystals, wherein the method further comprises soaking the bone-like portion of the prosthesis in water to dissolve the salt crystals.

Aspect 6: The method of aspect 5, wherein the salt crystals have a major dimension that is less than 100-300 micrometers.

Aspect 7: The method of any one of the preceding aspects, wherein filling the cartilage space with the material to form the cartilage-like portion of the prosthesis comprises filling the cartilage space with hydrogel, and irradiating the material to crosslink the hydrogel.

Aspect 8: The method of aspect 7 wherein the hydrogel comprises methacrylated hyaluronic acid (meHA)

Aspect 9: The method of aspect 7 or aspect 8, wherein the hydrogel is cell-laden.

Aspect 10: The method of aspect 9, wherein the hydrogel is cell-laden with between 10 million and 100 million cells per milliliter of hydrogel.

Aspect 11: The method of any one of the preceding aspects, wherein each of the first three dimensional model and the second three-dimensional model is created from an image of the at least a portion of the bone, wherein the image is captured with one of a computed tomography (CT) scan, magnetic resonance imaging (MRI), or a laser scan of an ex vivo sample.

Aspect 12: The method of aspect 11, wherein the image is captured with the laser scan of the ex vivo sample, wherein the bone is soaked in a solution to enhance cartilage contrast.

Aspect 13: The method of aspect 11 or aspect 12, further comprising: creating, based on the image of the bone and using at least one processor, the first three-dimensional model of the at least a portion of the bone; and creating, based on the image of the bone and using the at least one processor, the second three-dimensional model of the at least a portion of the bone and cartilage thereon.

Aspect 14: The method of any one of the preceding aspects, wherein each of the first three-dimensional model and the second three-dimensional model is a surface mesh.

Aspect 15: The method of aspect 13 or aspect 14, wherein each of the first three-dimensional model and the second three-dimensional model is provided as a. STL file.

Aspect 16: The method of any one of aspects 13-15, wherein creating the first three-dimensional model comprises using an edge collapse decimation to reduce a number of faces of the surface mesh of the first three-dimensional model.

Aspect 17: The method of any one of aspects 13-16, wherein creating the first three-dimensional model of the at least a portion of the bone comprises applying a Laplacian smoothing to the first three-dimensional model.

Aspect 18: The method of any one of aspects 13-17, wherein the bone defines a volume, wherein creating the first three-dimensional model of the at least a portion of the bone comprises deleting vertices of the surface mesh that, if the surface mesh and the bone were overlaid at a 1:1 scale, would be positioned within the volume of the bone.

Aspect 19: The method of any one of aspects 13-18, wherein creating the first three-dimensional model of the at least a portion of the bone comprises editing the surface mesh of the first three-dimensional model to remove any clinical damage of the bone.

Aspect 20: The method of aspect 19, wherein the clinical damage of the bone comprises a hole or an osteophyte.

Aspect 21: The method of any one of aspects 13-20, wherein creating the first three-dimensional model of the at least a portion of the bone comprises forming a fixation keel.

Aspect 22: The method of any one of aspects 13-20, wherein the bone has a shape, the method further comprising: cutting the bone to remove a portion thereof and leave a remaining portion of the bone, wherein creating the first three-dimensional model of the at least a portion of the bone comprises modifying an end of the first three-dimensional model so that the prosthesis formed from the first three-dimensional model cooperates with the remaining portion of the bone to form a coupled prosthesis having a shape matching the shape of the bone.

Aspect 23: The method of any one of aspects 13-22, wherein creating the second three-dimensional model of the at least a portion of the bone and cartilage thereon comprises translating a first portion of the surface mesh of the first three-dimensional model away from an opposing second portion of the surface mesh of the first three-dimensional model along an axis.

Aspect 24: The method of aspect 23, wherein translating the first portion of the surface mesh away from the second portion of the surface mesh along the axis comprises translating the first portion by between 0.25 mm and 1 mm.

Aspect 25: The method of any one of the preceding aspects, wherein the bone is a carpal bone.

Aspect 26: The method of aspect 25, wherein the bone is a trapezium bone.

Aspect 27: The method of any one of aspects 1-24, wherein the bone is a porcine accessory carpal.

Aspect 28: A prosthesis formed according to the method of any one of the preceding aspects.

Although several embodiments of the invention have been disclosed in the foregoing specification and the following appendices, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for forming a prosthesis having a bone-like portion and a cartilage-like portion, the method comprising:
    additively manufacturing a first positive mold in accordance with at least a portion of a first three-dimensional model of at least a portion of a bone;
    forming a first negative mold from the first positive mold;
    creating the bone-like portion of the prosthesis within the first negative mold;
    additively manufacturing a second positive mold of the bone and a cartilage from a second three-dimensional model, wherein a portion of the second three-dimensional model corresponds to a portion of the first three-dimensional model;
    forming a second negative mold from the second positive mold;
    positioning the bone-like portion of the prosthesis in the second negative mold so that the second negative mold and the bone-like portion of the prosthesis cooperatively define a cartilage space; and
    filling the cartilage space with a material to form the cartilage-like portion of the prosthesis.

2. The method of claim 1, wherein forming the negative mold from the first positive mold comprises forming the first negative mold from polydimethylsiloxane (PDMS).

3. The method of claim 1, wherein creating the bone-like portion comprises filling the first negative mold with a mixture comprising polycaprolactone (PCL) dissolved in chloroform and allowing the chloroform to evaporate from the mixture.

4. The method of claim 3, wherein the mixture further comprises sodium chloride crystals, wherein the method further comprises soaking the bone-like portion of the prosthesis in water to dissolve the salt crystals.

5. The method of claim 4, wherein the salt crystals have a major dimension that ranges from 100 to 300 micrometers.

6. The method of claim 1, wherein the bone-like portion contains a bone-promoting factor.

7. The method of claim 1, wherein filling the cartilage space with the material to form the cartilage-like portion of the prosthesis comprises filling the cartilage space with hydrogel, and irradiating the material to crosslink the hydrogel.

8. The method of claim 7, wherein the hydrogel comprises methacrylated hyaluronic acid (meHA).

9. The method of claim 7, wherein the hydrogel is cell-laden.

10. The method of claim 9, wherein the hydrogel is cell-laden with between 10 million and 100 million cells per milliliter of hydrogel.

11. The method of claim 1, wherein each of the first three dimensional model and the second three-dimensional model is created from an image of the at least a portion of the bone, wherein the image is captured with one of a computed tomography (CT) scan, magnetic resonance imaging (MRI), or a laser scan of an ex vivo sample.

12. The method of claim 11, wherein the image is captured with the laser scan of the ex vivo sample, wherein the bone is soaked in a solution to enhance cartilage contrast.

13. The method of claim 11, further comprising:
creating, based on the image of the bone and using at least one processor, the first three-dimensional model of the at least a portion of the bone; and
creating, based on the image of the bone and using the at least one processor, the second three-dimensional model of the at least a portion of the bone and cartilage thereon.

14. The method of claim 13, wherein each of the first three-dimensional model and the second three-dimensional model is a surface mesh.

15. The method of claim 14, wherein each of the first three-dimensional model and the second three-dimensional model is provided as a .STL file.

16. The method of claim 13, wherein creating the first three-dimensional model comprises using an edge collapse decimation to reduce a number of faces of the surface mesh of the first three-dimensional model.

17. The method of claim 13, wherein creating the first three-dimensional model of the at least a portion of the bone comprises applying a Laplacian smoothing to the first three-dimensional model.

18. The method of claim 13, wherein the bone defines a volume, wherein creating the first three-dimensional model of the at least a portion of the bone comprises deleting vertices of the surface mesh that, if the surface mesh and the bone were overlaid at a 1:1 scale, would be positioned within the volume of the bone.

19. The method of claim 13, wherein creating the first three-dimensional model of the at least a portion of the bone comprises editing the surface mesh of the first three-dimensional model to remove any clinical damage of the bone.

20. The method of claim 19, wherein the clinical damage of the bone comprises a hole or an osteophyte.

21. The method of claim 13, wherein creating the first three-dimensional model of the at least a portion of the bone comprises forming a fixation keel.

22. The method of claim 13, wherein the bone has a shape, the method further comprising:
cutting the bone to remove a portion thereof and leave a remaining portion of the bone,
wherein creating the first three-dimensional model of the at least a portion of the bone comprises modifying an end of the first three-dimensional model so that the prosthesis formed from the first three-dimensional model cooperates with the remaining portion of the bone to form a coupled prosthesis having a shape matching the shape of the bone.

23. The method of claim 13, wherein creating the second three-dimensional model of the at least a portion of the bone and cartilage thereon comprises translating a first portion of the surface mesh of the first three-dimensional model away from an opposing second portion of the surface mesh of the first three-dimensional model along an axis.

24. The method of claim 23, wherein translating the first portion of the surface mesh away from the second portion of the surface mesh along the axis comprises translating the first portion by between 0.25 mm and 1 mm.

25. The method of claim 1, wherein the bone is a carpal bone.

\* \* \* \* \*